(12) United States Patent
Hashida et al.

(10) Patent No.: US 10,987,232 B2
(45) Date of Patent: Apr. 27, 2021

(54) ARTIFICIAL KNEE JOINT REPLACEMENT OPERATION INSTRUMENT

(71) Applicant: KYOCERA Corporation, Kyoto (JP)

(72) Inventors: Masahiko Hashida, Kyoto (JP); Akinori Mori, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 75 days.

(21) Appl. No.: 16/335,606

(22) PCT Filed: Sep. 27, 2017

(86) PCT No.: PCT/JP2017/034968
§ 371 (c)(1),
(2) Date: Mar. 21, 2019

(87) PCT Pub. No.: WO2018/062279
PCT Pub. Date: Apr. 5, 2018

(65) Prior Publication Data
US 2019/0298543 A1 Oct. 3, 2019

(30) Foreign Application Priority Data

Sep. 28, 2016 (JP) .............................. JP2016-189481

(51) Int. Cl.
*A61F 2/46* (2006.01)
*A61B 17/16* (2006.01)
(Continued)

(52) U.S. Cl.
CPC .......... *A61F 2/461* (2013.01); *A61B 17/1675* (2013.01); *A61B 17/1764* (2013.01);
(Continued)

(58) Field of Classification Search
CPC ........................... A61F 2/461; A61B 17/1675
See application file for complete search history.

(56) References Cited

U.S. PATENT DOCUMENTS 7,862,553 B2   1/2011   Ewaschuk
8,377,044 B2   2/2013   Coe et al.
(Continued)

FOREIGN PATENT DOCUMENTS

JP   2007-021200 A   2/2007
JP   2013-013732 A   1/2013
(Continued)

*Primary Examiner* — Bruce E Snow
*Assistant Examiner* — Melissa A Hoban
(74) *Attorney, Agent, or Firm* — Volpe Koenig

(57) ABSTRACT

When using an artificial knee joint replacement operation instrument, the amount of labor required to attach a tibial insert trial to a patient is further reduced. An artificial knee joint replacement operation instrument has a tibial trial attachment instrument assembly used in an operation for replacing a patient's knee joint with an artificial knee joint. The tibial trial attachment instrument assembly includes a template to be attached to a tibia, a keel punch guide to be joined to the tibia via the template, a keel punch to be inserted into the tibia through the keel punch guide, a keel punch handle for operating the keel punch, and a tibial insert trial to be placed on the template, the tibial insert trial being separate from the template.

7 Claims, 20 Drawing Sheets

(51) Int. Cl.
  *A61B 17/17* (2006.01)
  *A61F 2/38* (2006.01)
  *A61B 17/92* (2006.01)
  *A61B 17/56* (2006.01)

(52) U.S. Cl.
  CPC .............. *A61B 17/56* (2013.01); *A61B 17/92* (2013.01); *A61F 2/38* (2013.01); *A61F 2/389* (2013.01); *A61F 2/46* (2013.01); *A61F 2/4684* (2013.01); *A61F 2/4603* (2013.01); *A61F 2002/4615* (2013.01)

(56) References Cited

U.S. PATENT DOCUMENTS

| | | |
|---|---|---|
| 8,852,197 B2 | 10/2014 | Waite, II et al. |
| 8,968,412 B2 | 3/2015 | Wogoman et al. |
| 2005/0075640 A1* | 4/2005 | Collazo ............... A61B 17/1675 606/86 R |
| 2007/0073247 A1 | 3/2007 | Ewaschuk |
| 2012/0158152 A1 | 6/2012 | Claypool et al. |
| 2013/0006253 A1 | 1/2013 | Waite, II et al. |
| 2013/0289569 A1* | 10/2013 | Wilkinson ......... A61B 17/1764 606/88 |
| 2013/0289570 A1* | 10/2013 | Chao ................ A61B 17/1764 606/88 |
| 2014/0052269 A1 | 2/2014 | Claypool et al. |
| 2015/0190243 A1 | 7/2015 | Claypool et al. |
| 2016/0324647 A1 | 11/2016 | Claypool et al. |
| 2017/0333214 A1* | 11/2017 | Hathaway ............. A61F 2/3859 |

FOREIGN PATENT DOCUMENTS

| | | |
|---|---|---|
| JP | 5559437 B2 | 7/2014 |
| WO | 2012/083280 A1 | 6/2012 |

* cited by examiner

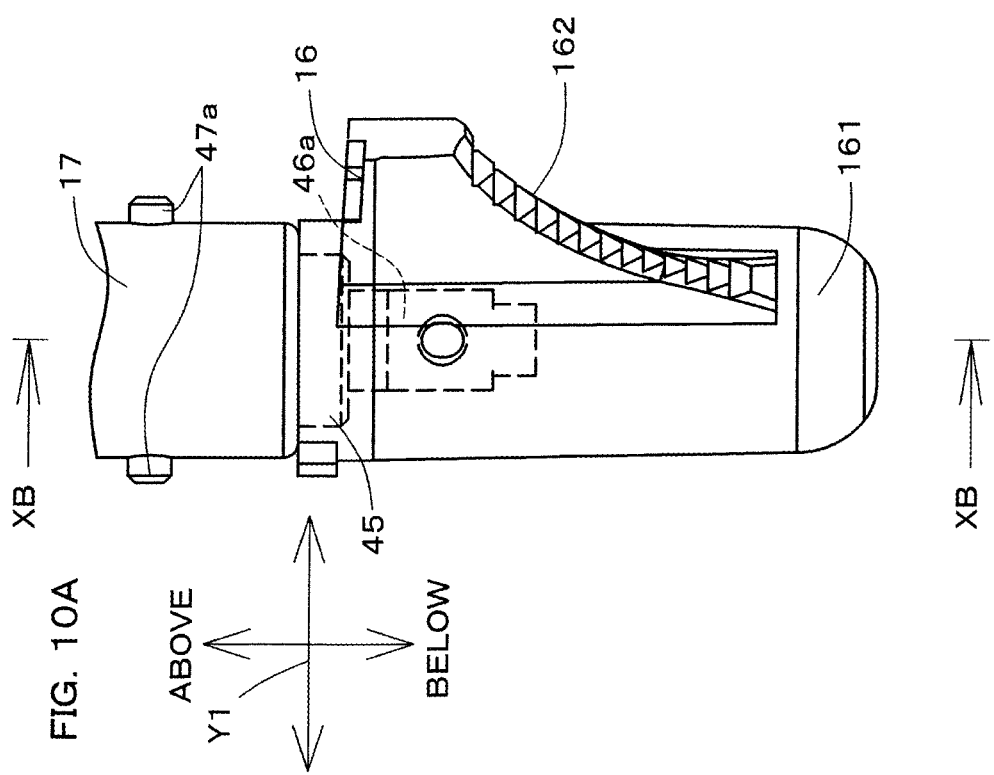
FIG. 10A
FIG. 10B

FIG. 13
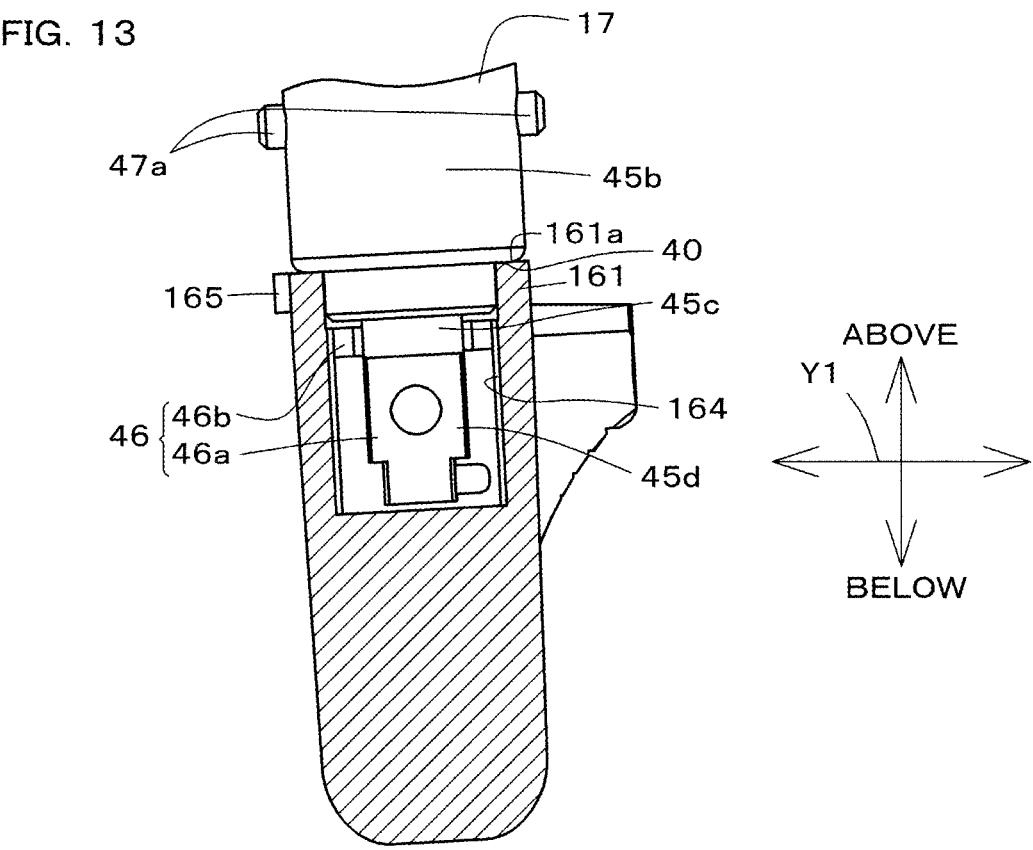
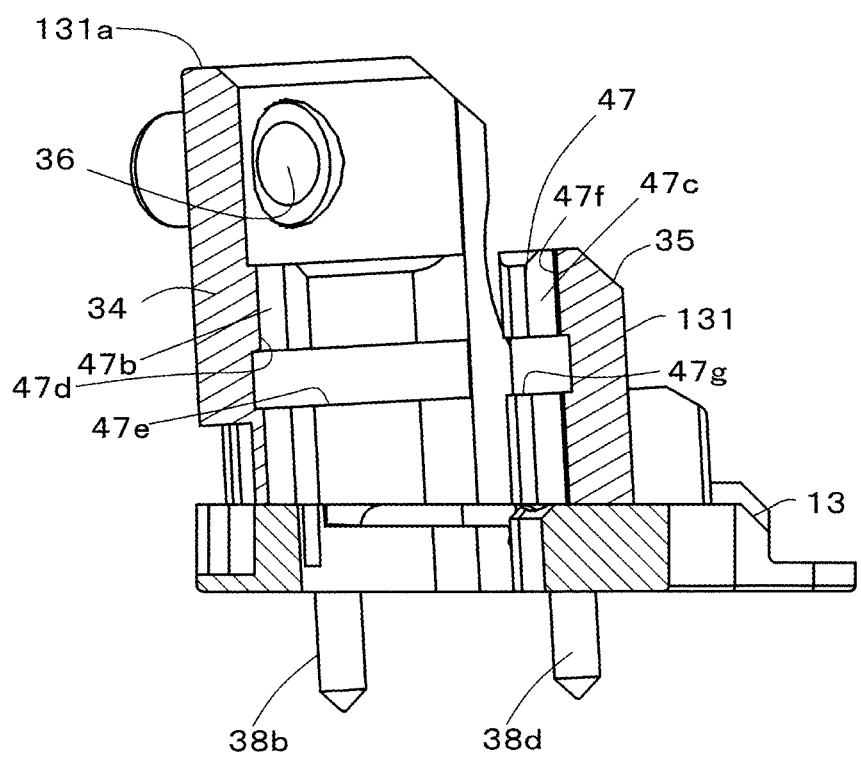

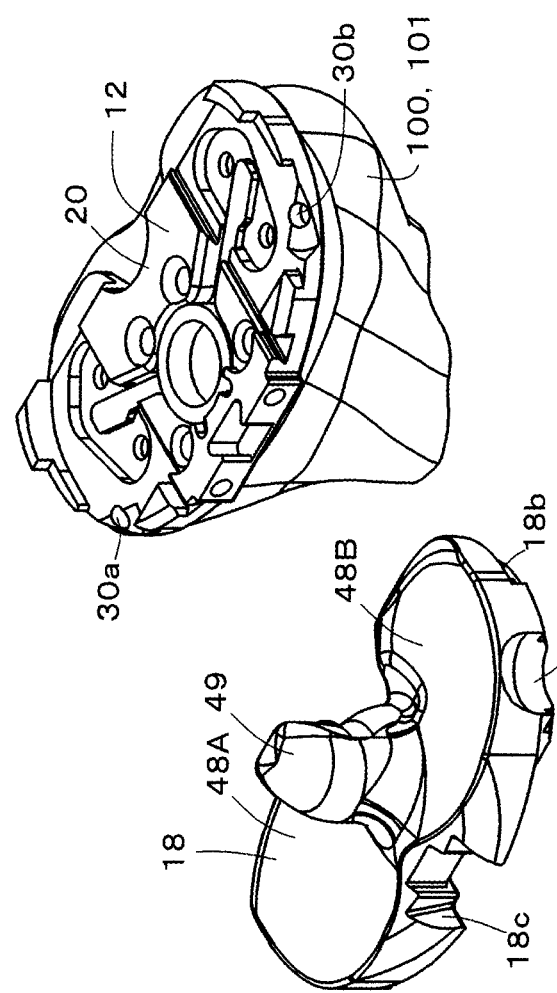

ARTIFICIAL KNEE JOINT REPLACEMENT OPERATION INSTRUMENT

TECHNICAL FIELD

The present invention relates to an artificial knee joint replacement operation instrument used in an operation for replacing a patient's knee joint with an artificial knee joint.

BACKGROUND ART

In an artificial knee joint replacement operation for replacing a patient's knee joint with an artificial knee joint, an operator performs osteotomy on a distal portion of a femur using a surgical instrument, and disposes a femoral component onto a cut bone surface formed as a result of the osteotomy. The operator also performs osteotomy on a proximal portion of a tibia using a surgical instrument, and disposes a tibial component onto a cut bone surface formed as a result of the osteotomy. When the tibial component is attached, a tibial trial is tentatively attached to the cut bone surface of the tibia. An optimal tibial component for the patient is determined by referencing this tibial trial (e.g. see Patent Documents 1 and 2).

In the configuration described in Patent Document 1, a base portion trial (12) attached to an alignment handle (16) is aligned with a proximal end (20) of a tibia (22). Next, a guide tower (14) is driven into the tibia (22). Then, a keel punch (220), to which an impaction handle (222) has been attached, is inserted into the guide tower (14), and the keel punch (220) is driven into the tibia (22). Here, the impaction handle (222) and the keel punch (220) are locked to each other due to a leading end of a lever (308) of the impaction handle (222) being caught on a lever-receiving notch (246), which is formed at an upper end of the keel punch (220).

Upon the impaction handle (222) and the keel punch (220) being inserted by a predetermined amount or more into the guide tower (14), the lever (308) is pressed by the guide tower (14). As a result, the lever (308) and the lever-receiving notch (246) of the keel punch (220) are unlocked from each other. At the same time, the lever (308) is caught on the guide tower (14). That is to say, the impaction handle (222) and the guide tower (14) are locked with each other. If the impaction handle (222) is pulled in this state, the guide tower (14) is pulled out of the tibia (22) together with the impaction handle (222). Meanwhile, the keel punch (220) is left in the tibia (20).

In the configuration described in Patent Document 2, a tibial bearing component (32A) is attached to a base plate (38A), which corresponds to the base portion trial (12). According to the above configuration, an optimal tibial component for a patient is determined.

CITATION LIST

Patent Document

Patent Document 1: JP 2013-13732A
Patent Document 2: JP 5559437B

DISCLOSURE OF THE INVENTION

Problem to be Solved by the Invention

In the above configuration, instruments (the guide tower (14) and the impaction handle (222)) for fixing the keel punch (220) to the tibia (20), and the tibial bearing component (32A) need to be prepared separately, and preparation of these instruments is laborious.

The invention of this application aims to further reduce the amount of labor required to attach a tibial insert trial to a patient, when using an artificial knee joint replacement operation instrument.

Means for Solving the Problem (1) An artificial knee joint replacement operation instrument according to an aspect of the present invention to achieve the above-stated object includes: a tibial trial attachment instrument assembly to be used in an operation for replacing a patient's knee joint with an artificial knee joint, the tibial trial attachment instrument assembly including: a template to be attached to the patient's tibia; a keel punch guide to be joined to the tibia via the template; a keel punch to be inserted into the tibia through the keel punch guide; a keel punch handle for operating the keel punch; and a tibial insert trial to be placed on the template, the tibial insert trial being separate from the template.

According to this configuration, the template, the keel punch guide, the keel punch, the keel punch handle, and the tibial insert trial are prepared as a single assembly. Accordingly, these instruments can be prepared collectively, which is less laborious than in the case of preparing these instruments separately. Accordingly, the amount of labor required to attach the tibial insert trial to a patient can be further reduced.

(2) There are cases where the artificial knee joint replacement operation instrument further includes a first connection mechanism configured to enable the keel punch handle and the keel punch to be attached to and detached from each other, and prevent the keel punch handle from coming out from the keel punch.

According to this configuration, the first connection mechanism can prevent the keel punch handle from coming out from the keel punch. Also, the keel punch handle can be disconnected from the keel punch when necessary. This makes it possible to suppress the case where the keel punch handle and the keel punch become hindrances. As a result, the amount of labor required to attach the tibial insert trial to a patient can be further reduced.

(3) There are cases where the first connection mechanism is configured to connect and disconnect the keel punch handle to and from the keel punch by moving the keel punch handle relative to the keel punch in a predetermined first direction that differs from an axial direction of the keel punch handle.

According to this configuration, connection and disconnection between the keel punch handle and the keel punch can be performed with a simple configuration in which the keel punch handle and the keel punch are relatively moved in the first direction. This makes it possible to further reduce the amount of labor required to attach the tibial insert trial to a patient.

(4) There are cases where the first direction is a rotational direction around an axis parallel to the axial direction.

According to this configuration, connection and disconnection between the keel punch handle and the keel punch can be performed with a simple configuration in which the keel punch handle and the keel punch are relatively rotated. This makes it possible to further reduce the amount of labor required to attach the tibial insert trial to a patient.

(5) There are cases where the first connection mechanism has a first protrusion formed in one of the keel punch handle and the keel punch, and a first connected portion formed in the other one of the keel punch handle and the keel punch, and the first protrusion is connected to and disconnected from the first connected portion by relative movement of the keel punch handle and the keel punch.

According to this configuration, connection and disconnection between the first protrusion and the first connected portion can be performed with a simple operation, that is, relative movement of the keel punch handle and the keel punch.

(6) There are cases where the first protrusion is provided at a leading end of the keel punch handle, and is formed to have a rectangular shape in a cross-section orthogonal to an axial direction of the keel punch handle, and the first connected portion includes a first projection formed on an inner-circumferential face of a tubular portion provided in the keel punch.

According to this configuration, the keel punch handle can be connected to the keel punch by causing the first protrusion, which has a protruding shape, to be caught on the first protrusion formed in a hole in the keel punch. Also, the aforementioned connection can be canceled by rotating the first protrusion relative to the first projection.

(7) There are cases where a pair of the first projections is provided at a pitch of 180 degrees on the inner-circumferential face of the tubular portion, and a hole portion having a cross-sectional shape that matches a cross-sectional shape of the first protrusion is formed within the tubular portion.

According to this configuration, since the first protrusion can be received by the pair of first projections, the connection strength between the keel punch handle and the keel punch can be further increased. With this configuration, the operator does not need to pay attention to the connection strength between the keel punch handle and the keel punch when handling the keel punch handle to which the keel punch has been attached. As a result, the amount of labor required to attach the tibial insert trial to a patient can be further reduced.

(8) There are cases where the artificial knee joint replacement operation instrument further includes a second connection mechanism for enabling the keel punch handle and the keel punch guide to be attached to and detached from each other, and integrally connecting the keel punch handle to the keel punch guide.

According to this configuration, the second connection mechanism enables the keel punch handle and the keel punch guide to be integrally connected. This makes it possible to pull out the keel punch guide using the keel punch handle. Also, the keel punch handle can be disconnected from the keel punch guide when necessary. This makes it possible to suppress the case where the keel punch handle and the keel punch guide become hindrances. As a result, the amount of labor required to attach the tibial insert trial to a patient can be further reduced.

(9) There are cases where the second connection mechanism is configured to connect and disconnect the keel punch handle to and from the keel punch guide by moving the keel punch handle relative to the keel punch guide in a predetermined second direction that differs from an axial direction of the keel punch handle.

According to this configuration, connection and disconnection between the keel punch handle and the keel punch guide can be performed with a simple configuration in which the keel punch handle and the keel punch guide are relatively moved in the second direction. This makes it possible to further reduce the amount of labor required to attach the tibial insert trial to a patient.

(10) There are cases where the second direction is a rotational direction around an axis parallel to the axial direction.

According to this configuration, connection and disconnection between the keel punch handle and the keel punch guide can be performed with a simple configuration in which the keel punch handle and the keel punch guide are relatively rotated. This makes it possible to further reduce the amount of labor required to attach the tibial insert trial to a patient.

(11) There are cases where the second connection mechanism includes a second protrusion formed in one of the keel punch handle and the keel punch guide, and a second connected portion formed in the other one of the keel punch handle and the keel punch guide, and the second protrusion is connected to and disconnected from the second connected portion by relative movement of the keel punch handle and the keel punch guide.

According to this configuration, a simple operation, that is, relative movement of the keel punch handle and the keel punch guide enables connection and disconnection between the second protrusion and the second connected portion.

(12) There are cases where the artificial knee joint replacement operation instrument further includes: a first connection mechanism configured to enable the keel punch handle and the keel punch to be attached to and detached from each other, and prevent the keel punch handle from coming out from the keel punch; and a second connection mechanism for enabling the keel punch handle and the keel punch guide to be attached to and detached from each other, and integrally connecting the keel punch handle to the keel punch guide, wherein connection between the keel punch handle and the keel punch through the first connection mechanism is canceled, and also the keel punch handle is connected-to the keel punch guide through the second connection mechanism.

According to this configuration, a single motion to displace the keel punch handle in one direction relative to the keel punch and the keel punch guide makes it possible to simultaneously cancel the connection between the keel punch handle and the keel punch through the first connection mechanism and connect the keel punch handle to the keel punch guide through the second connection mechanism. This makes it possible to further reduce the amount of labor required to attach the tibial insert trial to a patient, through a reduction in the amount of labor in handling the keel punch handle.

(13) There are cases where a direction in which the keel punch handle is displaced relative to the keel punch to connect the keel punch handle to the keel punch through the first connection mechanism and a direction in which the keel punch handle is displaced relative to the keel punch guide to connect the keel punch handle to the keel punch guide through the second connection mechanism are set to opposite directions.

According to this configuration, a configuration can be realized that makes it possible to simultaneously perform an operation to cancel the connection between the keel punch handle and the keel punch through the first connection mechanism and an operation to connect the keel punch handle to the keel punch guide through the second connection mechanism. It is thus possible to further reduce the amount of labor required to attach the tibial insert trial to a patient, through a reduction in the amount of labor in handling the keel punch handle.

(14) There are cases where the keel punch guide includes a tubular portion that is provided to allow the keel punch to pass therethrough and is arranged in alignment with the template, and a passage through which a template handle for operating the template passes when the template handle is removed from the template is formed in an outer-circumferential portion of the tubular portion.

According to this configuration, even in a state in which the space around the tibia is small because, for example, the template has been attached to a patient's tibia, the template handle can be removed from the template through the passage. This makes it possible to more easily operate the template handle. Accordingly, the amount of labor required to attach the tibial insert trial to a patient can be further reduced.

(15) There are cases where the tibial trial attachment instrument assembly includes a spacer capable of being inserted between the tibial insert trial and the template.

According to this configuration, the spacer for adjusting the height of the tibial insert trial from the template is included in the tibial trial attachment instrument assembly. This eliminates the need for a laborious operation to prepare the spacer separately from other members of the tibial trial attachment instrument assembly. Accordingly, the amount of labor required to attach the tibial insert trial to a patient can be further reduced.

Effects of the Invention

According to the present invention, the labor required to attach the tibial insert trial to a patient can be further reduced.

BRIEF DESCRIPTION OF THE DRAWINGS

FIG. 10A is a side view of a main portion, showing a state in which the keel punch has been connected to the keel punch handle. FIG. 10B is a cross-sectional view taken along a line XB-XB in FIG. 10A.

FIG. 13 is a side view showing a state in which the keel punch handle has been connected to the keel punch, together with the keel punch guide, and partially shows cross-sections of these components.

FIG. 14A is a perspective view showing a state in which the template is attached to the proximal portion of the tibia, before a tibial insert trial is attached to the template. FIG. 14B is a perspective view showing a state in which the template has been attached to the proximal portion of the tibia, and the tibial insert trial has been attached to the template.

DESCRIPTION OF EMBODIMENTS

Hereinafter, modes for carrying out the present invention will be described with reference to the drawings. Note that the present invention is broadly applicable as an artificial knee joint replacement operation instrument used in an operation for replacing a knee joint with an artificial knee joint.

Figure 1:
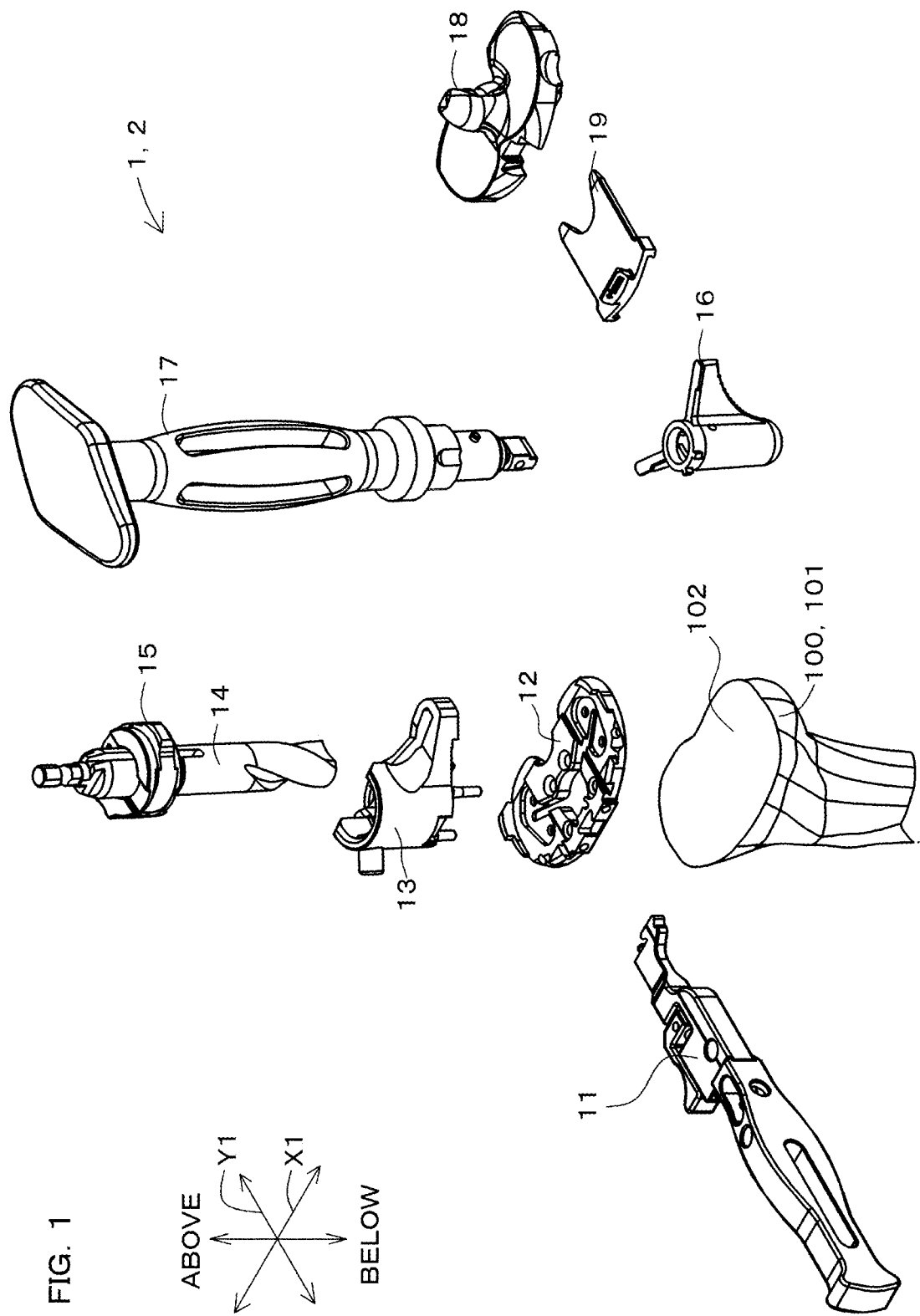
FIG. 1 is a perspective view showing an artificial knee joint replacement operation instrument according to the present invention and a portion of a patient's tibia.

FIG. 1 is a perspective view showing an artificial knee joint replacement operation instrument 1 according to the present invention, and a portion of a patient's tibia 100. Referring to FIG. 1, the artificial knee joint replacement operation instrument 1 is used in an artificial knee joint replacement operation for replacing a patient's knee joint with an artificial knee joint. This artificial knee joint replacement operation is used to restore normal functionality of a knee of a patient whose knee joint has deformed to a high degree due to gonarthrosis or chronic rheumatism, for example.

In the artificial knee joint replacement operation, osteotomy is performed on a proximal portion 101 of the patient's tibia 100, and a flat cut bone surface 102 is thus formed. Next, a tibial component suitable for the patient's tibia 100 is selected using a tibial insert trial 18. Also, in the artificial knee joint replacement operation, osteotomy is performed on a distal portion of the patient's femur (not shown), and thereafter, a femoral component suitable for the patient's femur is selected using a femoral trial. Then, the tibial component is attached to the proximal portion 101 of the tibia 100, and the femoral component is attached to the distal portion of the femur. The tibial component and the femoral component slide as the patient's knee bends, thereby achieving smooth bending of the knee.

In the present embodiment, the terms "inner side" and "outer side" refer respectively to the inner side and the outer side of the patient's knee that is to be subjected to an artificial knee joint replacement operation. An inward-outward direction X1 corresponds to the left-right direction of the patient. The "front" and the "rear" refer respectively to the front and the rear of the patient. "Above" and "below" refer respectively to above and below for the patient (lengthwise direction of the tibia 100). In this embodiment, each component of the artificial knee joint replacement operation instrument 1 is described based on a state of having been attached to the proximal portion 101 of the patient's tibia 100.

The artificial knee joint replacement operation instrument 1 includes a tibial trial attachment instrument assembly 2.

The tibial trial attachment instrument assembly 2 is an instrument assembly for attaching the tibial insert trial 18 to the tibia 100. Component of the tibial trial attachment instrument assembly 2 are accommodated in a single case, or are shipped as a single set from a factory, and are handled as a single set in a medical institution, for example.

The tibia trial attachment instrument assembly 2 has a template handle 11, a template 12 that is to be attached to the patient's tibia 100, a keel punch guide 13 to be joined to the tibia 100 via the template 12, a drill 14, a drill stopper 15, a keel punch 16 to be inserted into the tibia 100 through the keel punch guide 13, a keel punch handle 17 for operating the keel punch 16, and a tibial insert trial 18 that is separate from the template 12 and is to be placed on the template 12, and a spacer 19 that can be inserted between the tibial insert trial 18 and the template 12.

The above-listed components 11 to 19 of the tibial trial attachment instrument assembly 2 are made of a material such as metal or a synthetic resin. The above-listed components 11 to 19 are preferably made of a biocompatible material, and it is preferable that at least a portion that may come into contact with the patient is made of a biocompatible material.

Note that the tibial trial attachment instrument assembly 2 need only have any combination of at least two of the above-listed components 11 to 19, and is not limited to the above configuration. For example, in the artificial knee joint replacement operation instrument 1, at least one of the template handle 11, the drill 14, and the drill stopper 15 does not need to be included in the tibial trial attachment instrument assembly 2.

Figure 2:
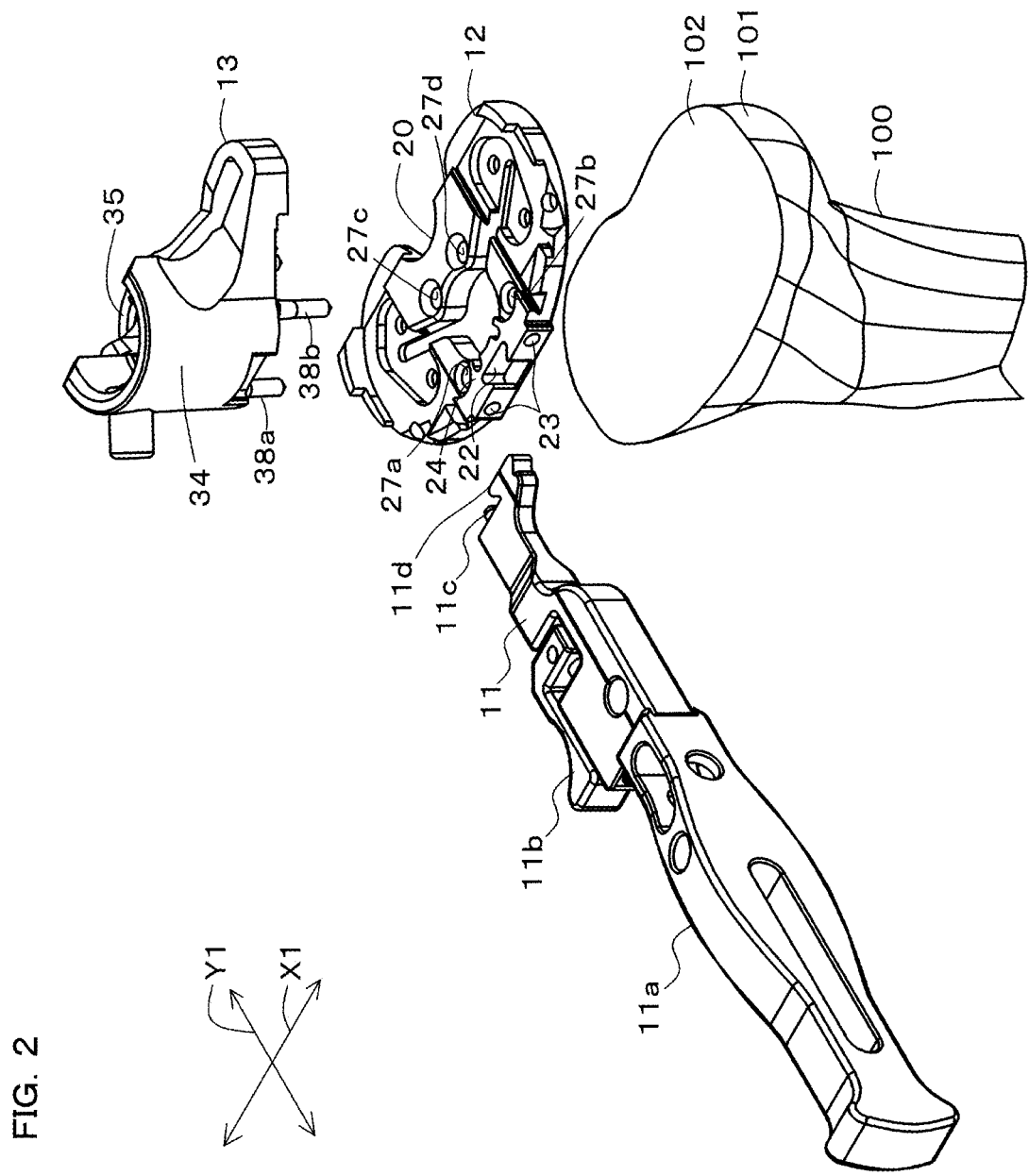
FIG. 2 is a perspective view of a template handle, a template, a keel punch guide, and the tibia.

FIG. 2 is a perspective view of the template handle 11, the template 12, the keel punch guide 13, and the tibia 100. Referring to FIGS. 1 and 2, the template handle 11 is used to operate the template 12. In a state in which an operator is holding the template handle 11, the template 12 is removably attached to a leading end of the template handle 11.

The template handle 11 includes a holding portion 11a, which is to be held by the operator, a lock lever 11b and a lock pin 11c, which are supported by the holding portion 11a, and a connecting portion 11d, which is formed at a leading end of the holding portion 11a.

The holding portion 11a is formed into an elongated bar shape, and is arranged in front of the proximal portion 101 of the tibia 100, for example. The lock lever 11b is supported by the holding portion 11a at a front-end side portion thereof such that the lock lever 11b can slide relative to the holding portion 11a in the lengthwise direction thereof. The lock pin 11c protrudes from the leading end of the holding portion 11a. The lock pin 11c is a shaft-shaped member, and is formed into a cylindrical shaft shape, for example. This lock pin 11c is configured to be displaced integrally with the lock lever 11b. The connecting portion 11d is arranged in on one side of the lock pin 11c. The connecting portion 11d is provided as a portion that is mated with a later-described connected portion 22 of the template 12. The connecting portion 11d is formed so as to increase in width as it extends toward a leading end thereof, for example.

As mentioned above, the template 12 is attached to the template handle 11. The template 12 is a plate-shaped member that is placed on the cut bone surface 102 of the proximal portion 101 of the tibia 100, on which the keel punch guide 13 or the tibial insert trial 18 is selectively placed, and through which the keel punch 16 is passed. The template 12 has a shape that substantially matches the shape of the cut bone surface 102 when seen in a plan view. Also, the template 12 is formed into a symmetrical shape in the inward-outward direction X1.

Figure 3:
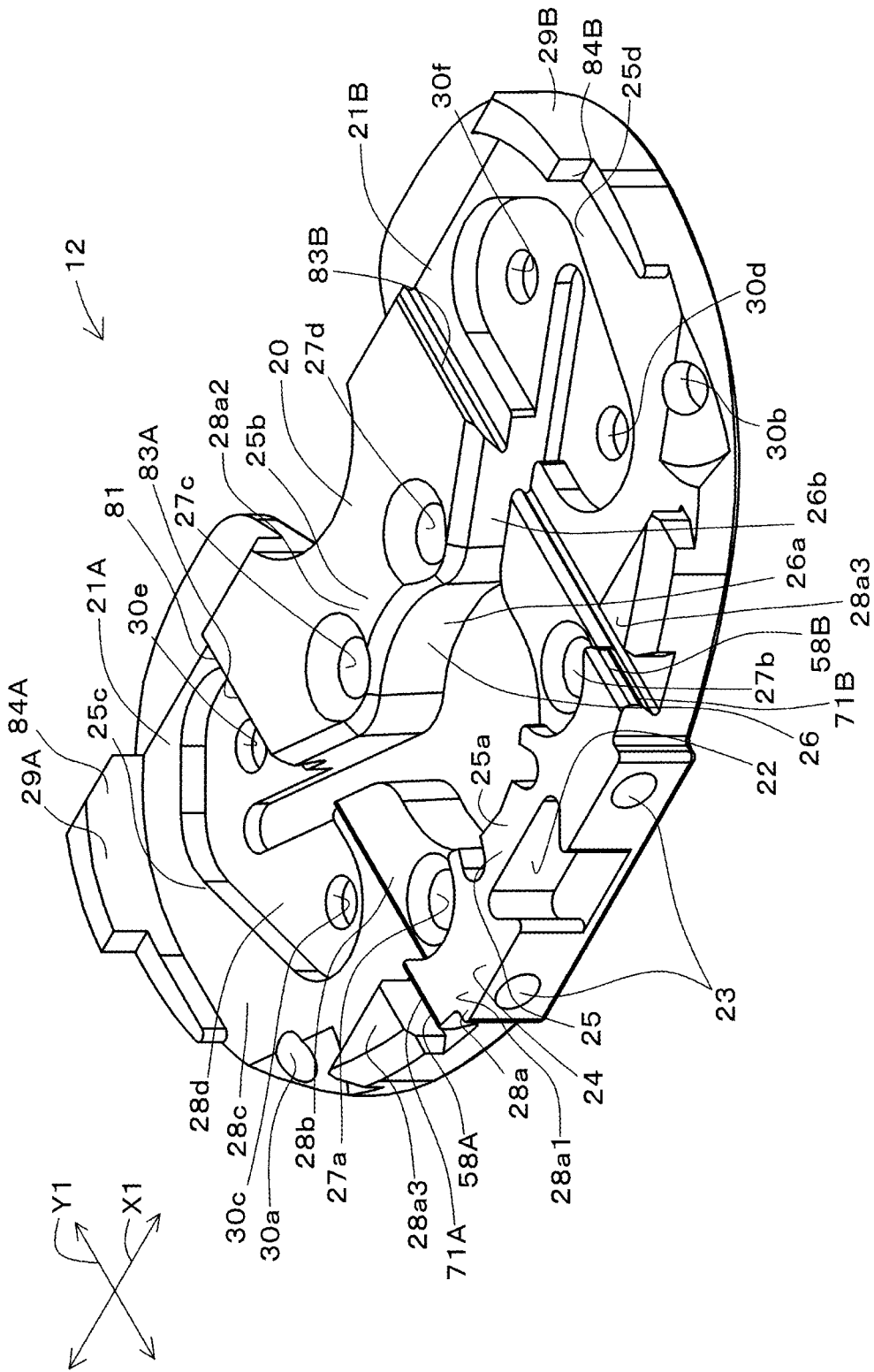
FIG. 3 is a perspective view of the template.
Figure 4A:
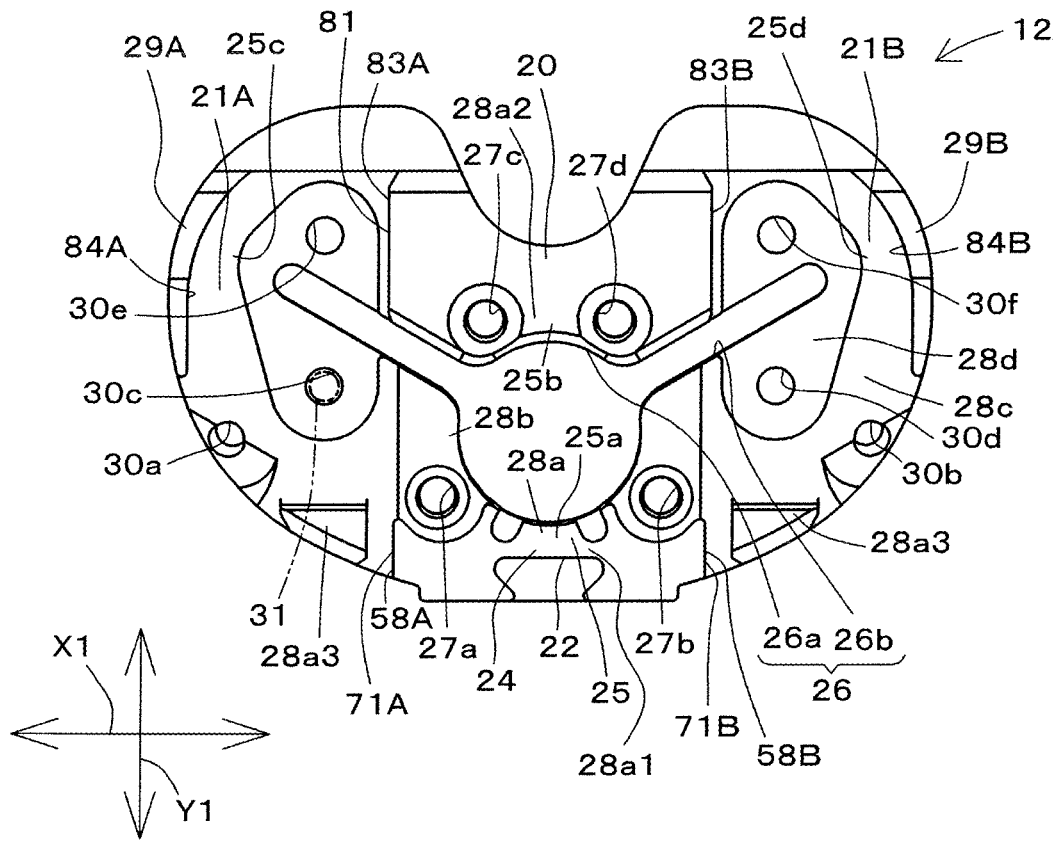
FIG. 4A is a plan view of the template.
Figure 4B:
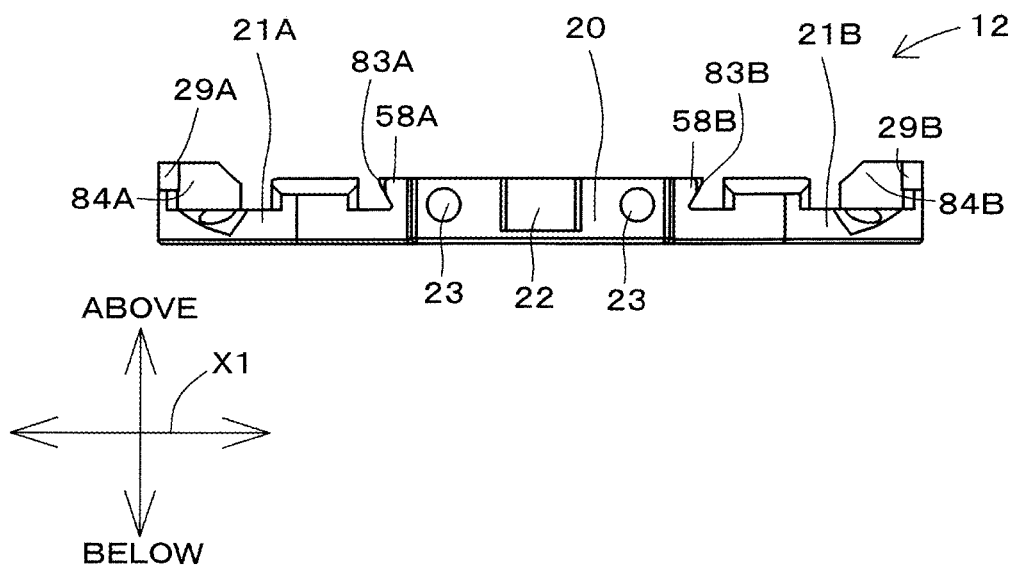
FIG. 4B is a front elevational view of the template.

FIG. 3 is a perspective view of the template 12. FIG. 4A is a plan view of the template 12. FIG. 4B is a front elevational view of the template 12. Referring to FIGS. 2, 3, 4A, and 4B, the template 12 has a central portion 20, side portions 21A and 21B, a connected portion 22 and two pin hole portions 23 that are arranged in a front portion of the template 12 for connection with the template handle 11, a first spacer receiving portion 24 for receiving the spacer 19, a guide receiving portion 25 for receiving the keel punch guide 13, a keel punch insertion hole portion 26, stud insertion hole portions 27a to 27d, and fixing pin insertion hole portions 30a to 30f.

The central portion 20 is formed over a predetermined range including the central portion of the template 12 in the inward-outward direction X1. The central portion 20 is formed over approximately the entire range of the template 12 in a front-rear direction Y1. A front portion of the central portion 20 extends substantially straight in the inward-outward direction X1. A recessed portion that is recessed forward is formed in a rear portion of the central portion 20. In the inward-outward direction X1, the length of the central portion 20 is set substantially the same as the length of the spacer 19. Also, two side portions 21A and 21B are arranged respectively on the right side and the left side of the central portion 20 in the inward-outward direction X1.

The side portions 21A and 21B are portions each having an edge portion formed into a curved shape that is close to an arc, when viewed in a plan view. In this embodiment, in the inward-outward direction X1, the length of each of the side portions 21A and 21B is set shorter than the length of the central portion 20. The connected portion 22 is provided at a front end of the central portion 20.

The connected portion 22 is formed into a hole shape that matches the shape of the connecting portion 11d at the leading end of the template handle 11, and is open in an upper face of the template 12. The pin hole portions 23 are formed respectively on the right side and the left side of the connected portion 22. The lock pin 11c of the template handle 11 is inserted into either one of the pin hole portions 23. According to this configuration, the connecting portion 11d of the template handle 11 is inserted into the connected portion 22, and the lock pin 11c is inserted into one of the pin hole portions 23, and thus the template 12 is connected to the template handle 11. Also, the template handle 11 can be removed from the template 12 by lifting up the template handle 11 from the template 12, in a state in which the lock pin 11c has been pulled out of the one of pin hole portions 23.

The template 12 includes first to fourth upper faces 28a to 28d.

In the inward-outward direction X1, the first upper face 28a is formed in front end portions of the side portions 21A and 21B of the template 12, and also in the central portion 20. The first upper face 28a is a flat face, and includes a front portion 28a1, a rear portion 28a2, and a pair of side portions 28a3 that are arranged in the same plane.

The front portion 28a1 of the first upper face 28a is provided in the central portion 20 as a face that is continuous with a front face of the central portion 20, and the connected portion 22 is open in the front portion 28a1. A rear end edge of the front portion 28a1 is formed into an arc shape to allow the keel punch 16 (see FIG. 1) to pass through. A rear portion 28a2 of the first upper face 28a is arranged rearward of the front portion 28a1 of the first upper face 28a. The rear portion 28a2 of the first upper face 28a is formed in the central portion 20, and extends rearward. A front end edge of the rear portion 28a2 of the first upper face 28a is formed into an arc shape to allow the keel punch 16 (see FIG. 1) to pass through. The side portions 28a3 of the first upper face 28a are provided in front end portions of the pair of side portions 21A and 21B, and are arranged next to the front portion 28a1 of the first upper face 28a in the inward-outward direction X1. The size of the side portions 28a3 of the first upper face 28a is set smaller than the size of the front portion 28a1 of the first upper face 28a.

The stud insertion hole portions 27a to 27d, through which studs 38a to 38d of the keel punch guide 13 are to pass, are formed in the first upper face 28a and the second upper face 28b. The stud insertion hole portions 27a and 27b are arranged in the second upper face 28b. The stud insertion hole portions 27c and 27d are arranged in the rear portion 28a2 of the first upper face 28a, near the front end edge of the rear portion 28a2.

The second upper face 28b is also formed in the central portion 20. The second upper face 28b is arranged between the front portion 28a1 and the rear portion 28a2 of the first upper face 28a. The height position of the second upper face 28b is set lower than the position of the first upper face 28a. The second upper face 28b is formed into a symmetrical shape in the inward-outward direction X1. An inner end edge of the second upper face 28b in the inward-outward direction X1 is formed into an arc shape to allow the keel punch 16 (see FIG. 1) to pass through.

The third upper face 28c is formed on the outer side of the second upper face 28b in the inward-outward direction X1. The third upper face 28c is formed into a symmetrical shape in the inward-outward direction X1, and forms a portion of upper faces of the pair of side portions 21A and 21B. The height position of the third upper face 28c is set lower than the position of the second upper face 28b.

Side end walls 29A and 29B are formed in respective end portions of the third upper face 28c in the inward-outward direction X1. The side end walls 29A and 29B are wall portions that are arranged close to a rear portion of the third upper face 28c, and protrude upward. Each of the side end walls 29A and 29B has a step portion in an intermediate portion thereof, and the height position of rear portions of the side end walls 29A and 29B is set higher than the height position of front portions of the side end walls 29A and 29B.

The fourth upper face 28d is arranged so as to be surrounded by the third upper face 28c when seen in a plan view.

The fourth upper face 28d is formed into a symmetrical shape in the inward-outward direction X1, and forms a portion of the upper faces of the pair of side portions 21A and 21B. The height position of the fourth upper face 28d is set lower than the position of the third upper face 28c.

Out of the first upper face 28a to the fourth upper face 28d that have the above configuration, the first upper face 28a includes a first spacer receiving portion 24. The first spacer receiving portion 24 is provided as a portion for receiving the spacer 19 (see FIG. 19) from below the spacer 19. The first spacer receiving portion 24 is formed by at least a portion of the first upper face 28a. In this embodiment, the first spacer receiving portion 24 is provided in the front portion 28a1 and the rear portion 28a2 of the first upper face 28a. In this embodiment, the first spacer receiving portion 24 is constituted by portions of the front portion 28a1 and the rear portion 28a2 of the first upper face 28a of the central portion 20, namely portions thereof on which the spacer 19 can be put. According to this configuration, the spacer 19 is received by the first spacer receiving portion 24 in two portions on the front end side and rear end side, and can thus be received in a more stable orientation by the template 12. The guide receiving portion 25 is arranged adjacent to the first spacer receiving portion 24. The guide receiving portion 25 is provided as a portion for receiving the keel punch guide 13.

Figure 5:
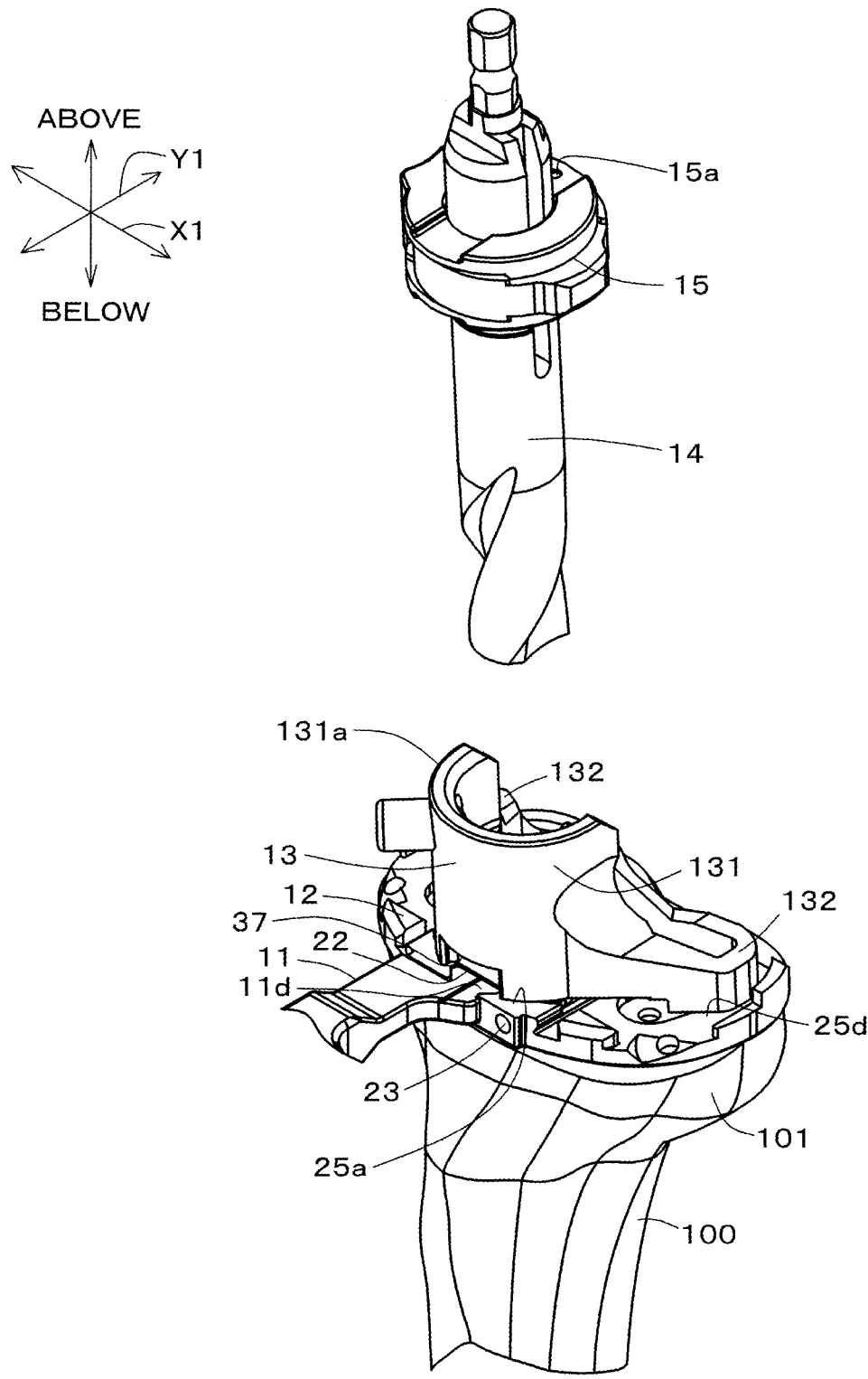
FIG. 5 is a perspective view showing a state in which the template and the keel punch guide have been attached to a proximal portion of the tibia.

The guide receiving portion 25 has a front portion 25a, a rear portion 25b, and side portions 25c and 25d, and is configured to support the keel punch guide 13 in a stable orientation by supporting the keel punch guide 13 at four points (see FIG. 5).

The front portion 25a of the guide receiving portion 25 is formed in the front portion 28a1 of the first upper face 28a. In this embodiment, the rear portion 25b of the guide receiving portion 25 is formed in the rear portion 28a2 of the first upper face 28a. In this embodiment, the side portions 25c and 25d of the guide receiving portion 25 are formed in the third upper face 28c. The side portions 25c and 25d of the guide receiving portion 25 are constituted by the third upper face 28c on which the keel punch guide 13 can be placed, around the boundary with the fourth upper face 28d. The keel punch insertion hole portion 26 is formed adjacent to the guide receiving portion 25 having the above configuration.

The keel punch insertion hole portion 26 is formed as a portion through which the keel punch 16 (see FIG. 1) passes when being inserted into the proximal portion 101 of the tibia 100. The keel punch insertion hole portion 26 has a circular portion 26a and a pair of wing-shaped portions 26b that extend from this circular portion. The circular portion 26a is a hole portion surrounded by the rear end edge of the front portion 28a1 of the first upper face 28a, the front end edge of the rear portion 28a2, and the inner end edge of the second upper face 28b. The two wing-shaped portions 26b are substantially straight portions, when seen in a plan view, and extend from the second upper face 28b to the fourth upper face 28d. According to the above configuration, the keel punch insertion hole portion 26 is formed into a substantially V-shape when seen in a plan view. The fixing pin insertion hole portions 30a to 30f are formed at positions that do not overlap the keel punch insertion hole portion 26.

The fixing pin insertion hole portions 30a to 30f are provided as penetrating portions through which fixing pins 31 (fixing member; indicated by a dash-double dot line in FIG. 4) for fixing the template 12 to the proximal portion 101 of the tibia 100 pass. A plurality of fixing pin insertion hole portions 30a to 30f are provided, and are provided in six portions in this embodiment. This embodiment employs a configuration in which the positions of the fixing pin insertion hole portions 30a to 30f differ from the position of the spacer 19 (the first spacer receiving portion 24) in the inward-outward direction X1.

The fixing pin insertion hole portions 30a and 30b are arranged at end portions, in the inward-outward direction X1, of front portions of the pair of side portions 21A and 21B of the template 12, and are open in the third upper face 28c. The fixing pin insertion hole portions 30c and 30d are arranged in the fourth upper face 28d close to front portions thereof in the pair of side portions 21A and 21B of the template 12, and are open in the fourth upper face 28d. The fixing pin insertion hole portions 30e and 30f are arranged in the fourth upper face 28d close to rear portions thereof in pair of side portions 21A and 21B of the template 12, and are open in the fourth upper face 28d.

Figure 6A:
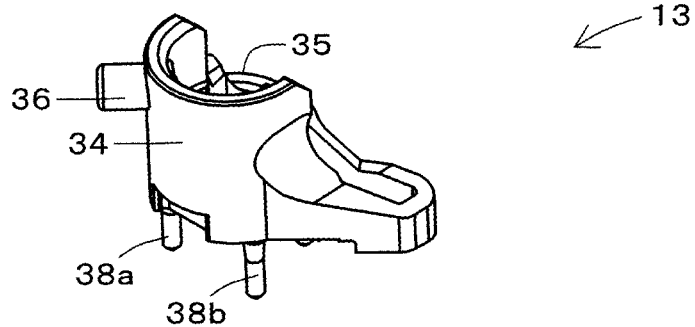
FIGS. 6A and 6B are perspective views of the keel punch guide.
Figure 6B:
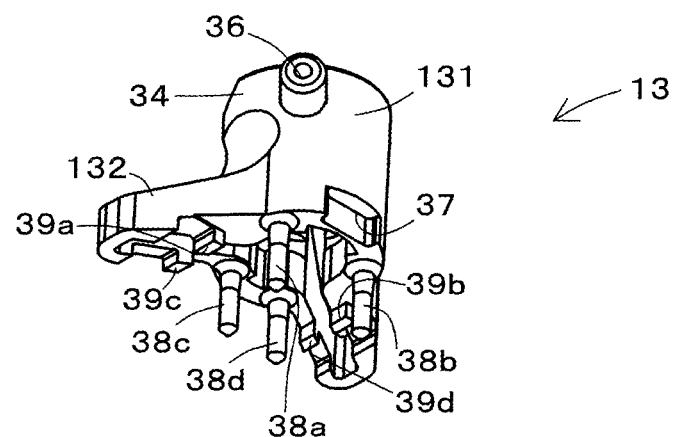
Figure 6C:
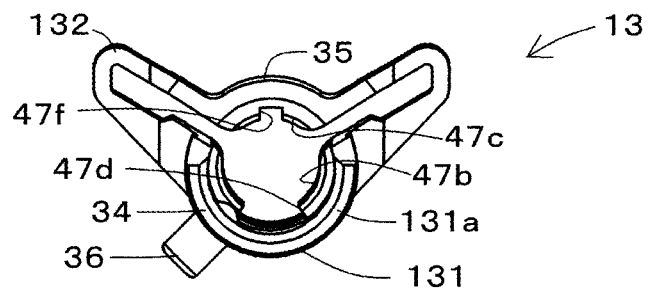
FIG. 6C is a plan view of the keel punch guide.
Figure 6D:
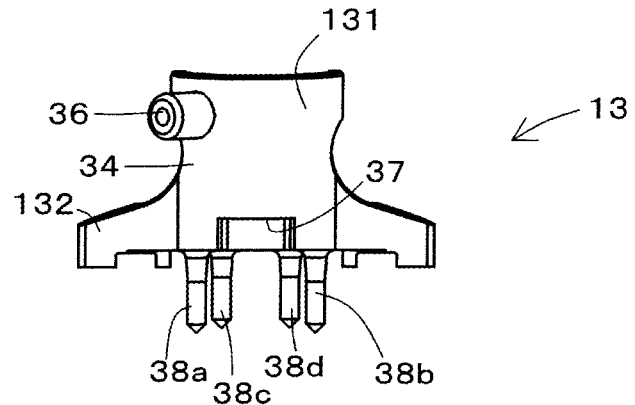
FIG. 6D is a front elevational view of the keel punch guide.

FIG. 5 is a perspective view showing a state in which the template 12 and the keel punch guide 13 have been attached to the proximal portion 101 of the tibia 100. FIGS. 6A and 6B are perspective views of the keel punch guide 13. FIG. 6C is a plan view of the keel punch guide 13. FIG. 6D is a front elevational view of the keel punch guide 13.

Referring to FIGS. 3, 5, and 6A to 6D, the keel punch guide 13 is attached to the template 12 in a state of having been placed on the cut bone surface 102 of the tibia 100. The keel punch guide 13 is a member for guiding the keel punch 16 when the keel punch 16 is inserted into the proximal portion 101. The keel punch guide 13 is formed into a V-shape when seen in a plan view.

The keel punch guide 13 includes a tubular portion 131 and a pair of wing portions 132, which are provided to allow the keel punch 16 to pass therethrough and are arranged in alignment with the template 12.

The tubular portion 131 is provided as a portion through which a tubular portion 161 of the keel punch 16 is to pass. In this embodiment, the tubular portion 131 is formed into a cylindrical shape. The tubular portion 131 includes a high-wall portion 34, which is formed on the front side of the keel punch guide 13, and a low-wall portion 35, which is formed on the rear side of the keel punch guide 13.

The high-wall portion 34 is a portion formed into an arc shape corresponding to approximately two-thirds of a circle, when seen in a plan view, and is formed into a shape that protrudes forward. A ball plunger 36, which serves as a positioning mechanism, is provided in the high-wall portion 34. The ball plunger 36 is provided to define the position of the keel punch handle 17 (see FIG. 1) in the rotational direction, relative to the keel punch guide 13. The ball plunger 36 has a configuration in which a spring and a ball are accommodated in a housing that protrudes from the high-wall portion 34 toward an outer-circumferential face of the high-wall portion 34. The ball in the ball plunger 36 is partially exposed in an inner-circumferential face of the high-wall portion 34. When subjected to an applied pressure, the ball in the ball plunger 36 withdraws into the housing against elastic repulsive force of the spring. A passage 37 is formed in a lower end portion of a front end portion of the outer-circumferential portion of the high-wall portion 34.

The passage 37 is a portion through which the connecting portion 11d of the template handle 11 for operating the template 12 passes when the template handle 11 is removed from the template 12. This passage 37 is arranged above the connected portion 22 of the template 12 when the keel punch guide 13 is attached to the template 12. The passage 37 is formed into a groove shape that extends upward from a lower end of the high-wall portion 34, and is open forward. The height and the width (the length in the inward-outward direction X1) of the passage 37 are set such that the connecting portion 11d of the template handle 11 can pass. The low-wall portion 35 is arranged rearward of the high-wall portion 34.

The low-wall portion 35 is a portion formed into an arc shape corresponding to approximately one-thirds of a circle, when seen in a plan view, and is formed into a shape that protrudes rearward. The height of the low-wall portion 35 is set lower than the height of the high-wall portion 34. The high-wall portion 34 and the low-wall portion 35 are connected to each other via the pair of wing portions 132.

The pair of wing portions 132 are provided as portions through which a later-described pair of wing portions 162 of the keel punch 16 passes. The pair of wing portions 132 is formed symmetrically in the inward-outward direction X1. Each of the wing portions 132 has a shape that extends rearward and outward in the inward-outward direction X1 from a corresponding end portion of the high-wall portion 34 in the inward-outward direction X1, and then extends forward and inward in the inward-outward direction X1 to be connected to a corresponding end portion of the low-wall portion 35. Upper faces of the wing portions 132 extend such that the height positions thereof are lower as they extend farther from the tubular portion 131. Lower faces of the wing portions 132 are partially flat.

Studs 38a to 38d are formed in a bottom face of the tubular portion 131. The studs 38a to 38d are provided to fix the keel punch guide 13 to the proximal portion 101 of the tibia 100, and are formed into shaft shapes extending downward from the tubular portion 131 so as to be able to be stuck into the proximal portion 101. The studs 38a and 38b are formed in the high-wall portion 34 of the tubular portion 131, and are arranged so as to be able to pass through the corresponding stud insertion hole portions 27a and 27b in the template 12. The studs 38c and 38d are formed in the low-wall portion 35 of the tubular portion 131, and are arranged so as to be able to pass through the corresponding stud insertion hole portions 27c and 27d of the template 12.

The keel punch guide 13 is supported by the template 12, with the studs 38a to 38d fixed to the tibia 100. Specifically, at a bottom face of the high-wall portion 34 of the tubular portion 131, a portion around the passage 37 is received by the front portion 25a (the first spacer receiving portion 24) of the guide receiving portion 25 of the template 12. Also, at a bottom face of the low-wall portion 35 of the tubular portion 131, a portion around the studs 38c and 38d is received by the rear portion 25b (the first spacer receiving portion 24) of the guide receiving portion 25 of the template 12. Bottom faces of leading end portions of the pair of wing portions 132 of the keel punch guide 13 are received by the side portions 25c and 25d of the guide receiving portion 25.

Positioning protrusions 39a to 39d for positioning the keel punch guide 13 on the template 12 are formed in a bottom face of the keel punch guide 13. The positioning protrusions 39a and 39b are portions that protrude downward from bottom faces of front portions of the pair of wing portions 132. These positioning protrusions 39a and 39b are attached at positions at which the positioning protrusions 39a and 39b can sandwich the central portion 20 of the template 12 in the inward-outward direction X1. The positioning protrusions 39c and 39d are portions that protrude downward from bottom faces of rear portions of the pair of wing portions 132. These positioning protrusions 39c and 39d are attached at positions at which the positioning protrusions 39c and 39d can sandwich the central portion 20 of the template 12 in the inward-outward direction X1.

According to the above configuration, as a result of the positioning protrusions 39a and 39b and the positioning protrusions 39c and 39d being arranged so as to sandwich the central portion 20, the keel punch guide 13 is positioned in the inward-outward direction X1 relative to the template 12. In a state in which the keel punch guide 13 is arranged on the template 12, a hole portion is formed in the proximal portion 101 of the tibia 100 by the drill 14.

The drill 14 is formed into a shaft shape, and has a diameter that allows the drill 14 to pass through the tubular portion 131 of the keel punch guide 13. A cutter portion is formed at a leading end of the drill 14, and is configured to cut the proximal portion 101 of the tibia 100. A connecting portion, which is to be connected to a driving source such as an electric actuator (not shown), is formed at a base end portion of the drill 14. The stopper 15 is disposed in an intermediate portion of the drill 14 on the base end side. The stopper 15 is provided to define the depth to which the drill 14 is inserted into the tubular portion 131 of the keel punch guide 13, i.e. the depth to which the drill 14 is inserted into the proximal portion 101 of the tibia 100. The stopper 15 is provided as a cylindrical element that is removable from the drill 14, and has a cylindrical member and a holding member that are connected to each other in a loose-fit state, via a shaft portion 15a (see FIG. 5). The holding portion has a pair of ring-shaped portions that sandwich the cylindrical member in the thickness direction, and a connecting portion that integrally connects the two ring-shaped portions to each other. The connecting portion is configured to integrally connect portions of outer-circumferential edge portions of the two ring-shaped portions to each other, in the axial direction of the cylindrical portion. The cylindrical member is held by the holding member, in a state of being sandwiched by the pair of ring-shaped portions of the holding member. An elongated hole, into which the shaft portion 15a is inserted in a loose-fit state, is provided in the cylindrical member. In a state in which the cylindrical member is sandwiched and held between the pair of ring-shaped portions of the holding member, the shaft portion 15a is fixed to the holding member at a position at which the shaft portion 15a is inserted into the elongated hole in the cylindrical member. Thus, the cylindrical member is connected, in a loose-fit state, to the holding member via the shaft portion 15a. A protrusion is provided on an inner-circumferential face of the cylindrical member, and is slidably fitted into a groove that is provided on an outer-circumferential face of a portion of the drill 14 on the base end side and extends in the axial direction of the drill 14. Note that an inner hole of the cylindrical member is configured as an elliptical hole, with a direction in which the protrusion extends serving as a major axis direction.

The stopper 15 can be removably disposed onto the drill 14 by inserting the portion of the drill 14 on the base end side into inner holes of the pair of ring-shaped portions of the holding portion and the inner hole of the cylindrical member, in a state in which the protrusion on the inner-circumferential face of the cylindrical member is fitted into the groove in the drill 14. The groove in the drill 14 is provided with a mating hole, which is recessed inward into the drill 14 at a predetermined position on a bottom portion of the groove. The stopper 15 is positioned in the axial direction relative to the drill 14 at a position corresponding to the aforementioned mating hole, in a state in which the portion of the drill 14 on the base end side has been inserted in the inner holes of the pair of ring-shaped portions and the inner hole of the cylindrical member. More specifically, an operation is performed to relatively move the cylindrical member with respect to the holding member and the drill 14 to push the cylindrical member toward the axis of the drill 14 so as to mate the protrusion on the inner-circumferential face of the cylindrical member with the aforementioned mating hole. At this time, the shaft portion 15a fixed to the holding member is inserted, in a loose-fit state, in the elongated hole in the cylindrical member, and the portion of the drill 14 on the base end side is inserted in the elliptical hole inside the cylindrical member. Accordingly, relative movement of the cylindrical member with respect to the drill 14 is allowed. Then, the protrusion on the inner-circumferential face of the cylindrical member of the stopper 15 is mated with the mating hole in the drill 14, and thus, the stopper 15 is positioned in the axial direction relative to the drill 14. The drill 14 is inserted into the keel punch guide 13 until the stopper 15 comes into contact with an opening edge portion 131a of the high-wall portion 34 of the tubular portion 131 of the keel punch guide 13. After a preparatory hole has been formed in the proximal portion 101 of the tibia 100 by the drill 14, the keel punch 16 attached to the keel punch handle 17 is inserted, through the keel punch guide 13, into the proximal portion 101 of the tibia 100, as shown in FIG. 7.

Figure 7:
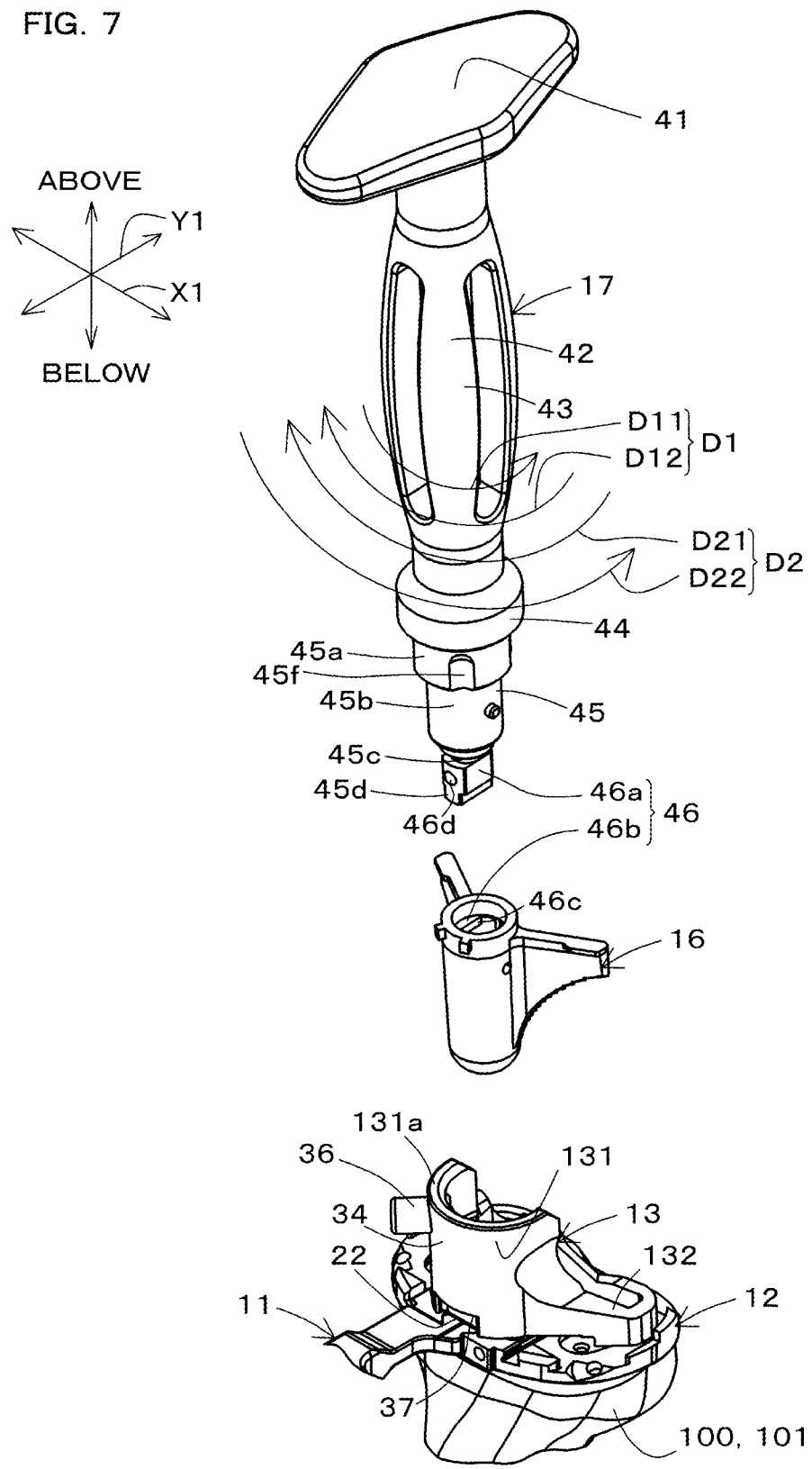
FIG. 7 is a perspective view showing the template handle, the template, a keel punch handle, the keel punch guide, and a keel punch, together with the tibia.
Figure 8A:
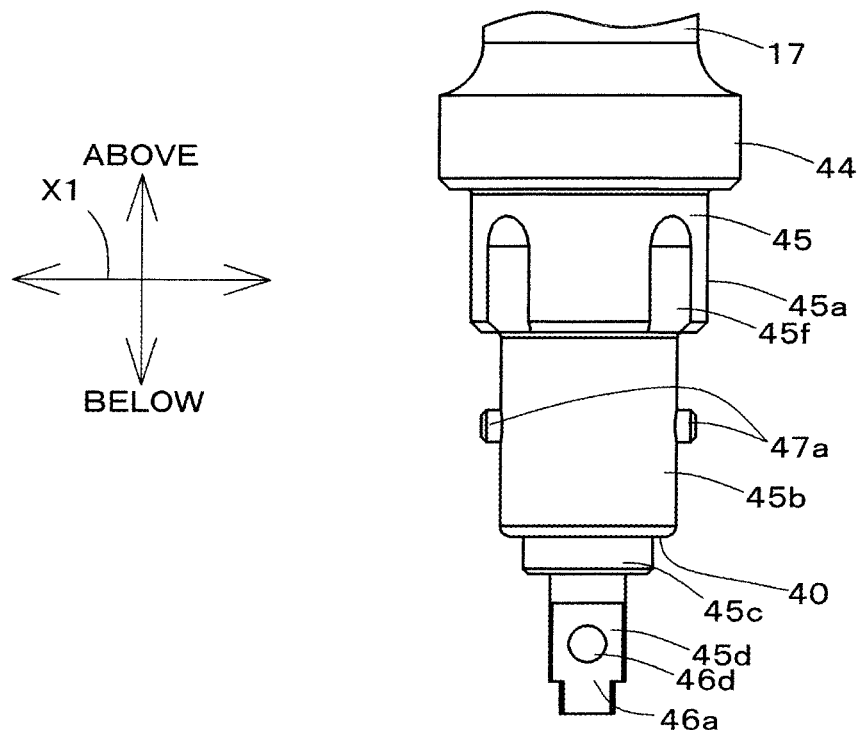
FIG. 8A is a side view of a main portion of the keel punch handle.
Figure 8B:
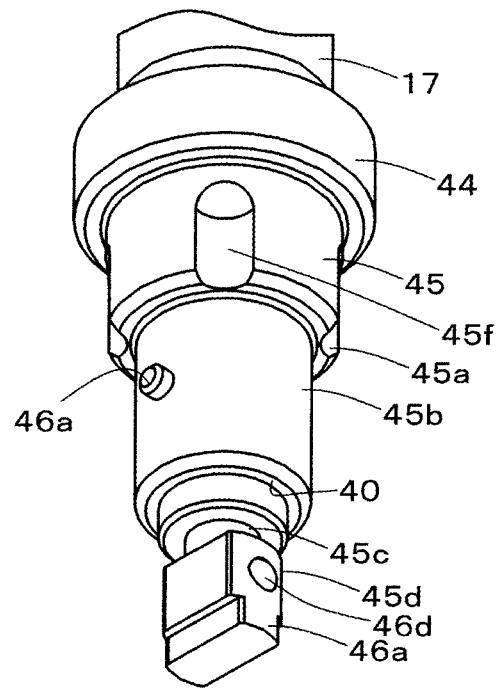
FIG. 8B is a perspective view of a main portion of the keel punch handle.

FIG. 7 is a perspective view showing the template handle 11, the template 12, the keel punch handle 17, the keel punch guide 13, and the keel punch 16, together with the tibia 100. FIG. 8A is a side view of a main portion of the keel punch handle 17. FIG. 8B is a perspective view of the main portion of the keel punch handle 17. Referring to FIGS. 7, 8A, and 8B, the keel punch handle 17 is used by an operator to operate the keel punch 16, and is also used by an operator to operate the keel punch guide 13. The keel punch handle 17 is an elongated member that extends axially.

The keel punch handle 17 has a flat portion 41 and a shaft portion 42.

The flat portion 41 is a flat plate-shaped portion formed in a base end portion of the keel punch handle 17, and extends orthogonally to the axial direction of the shaft portion 42. The flat portion 41 is a portion that is to be hit with a hammer by an operator when driving the keel punch 16 into the tibia 100 using the hammer, for example. The shaft portion 42 extends downward from the flat portion 41.

The shaft portion 42 has a grip portion 43, a second stopper 44, and an insertion end portion 45 that is formed on a leading end side of the second stopper 44.

The grip portion 43 is an elongated portion that is to be gripped by an operator, and an intermediate portion, in the axial direction, of the grip portion 43 bulges radially outward. The flat portion 41 is arranged in a base end portion of the grip portion 43, and the second stopper 44 is arranged in a leading end portion of the grip portion 43.

The second stopper 44 is provided as a circular plate-shaped portion that is to be received by the opening edge portion 131a of the tubular portion 131, and extends in a direction orthogonal to the axial direction of the keel punch handle 17. As a result of the second stopper 44 being received by the opening edge portion 131a, the position of the keel punch handle 17 in the axial direction relative to the keel punch guide 13 is defined.

The insertion end portion 45 includes a portion that is to be inserted into the tubular portion 161 of the keel punch 16. The insertion end portion 45 is provided as a portion that is to be inserted into the tubular portion 131 of the keel punch guide 13.

The insertion end portion 45 has first to fourth portions 45a to 45d.

The first portion 45a is a circular column-shaped portion that is continuous with the second stopper 44. Connected portions 45f are provided on an outer-circumferential face of the first portion 45a. The connected portions 45f are groove-shaped portions into which the ball in the ball plunger 36, which is a mechanism for positioning the keel punch guide 13, is fitted. The connected portions 45f extend in the axial direction of the keel punch handle 17, and are open in a lower end face of the first portion 45a. One or more (in this embodiment, four) connected portions 45f are provided at an even pitch in the circumferential direction of the first portion 45a.

When the ball in the ball plunger 36 has entered a connected portion 45f, and the value of the torque that acts on the keel punch handle 17 is a predetermined value or less, the ball in the ball plunger 36 restricts relative rotation of the keel punch guide 13. The second portion 45b extends from a leading end of the first portion 45a.

The second portion 45b is formed into a circular column shape with a diameter smaller than the diameter of the first portion 45a, and is configured to be arranged within the tubular portion 131 of the keel punch guide 13. A leading end face of the second portion 45b includes a first stopper 40, which is to be received by the opening edge portion 161a of the tubular portion 161 of the keel punch 16. The first stopper 40 is a flat face. The third portion 45c extends from a leading end of the second portion 45b.

The third portion 45c is a narrow shaft-shaped portion, and has a diameter that is set smaller than the diameter of the second portion 45b. The fourth portion 45d is formed at a leading end of the third portion 45c. The fourth portion 45d constitutes a leading end portion of the keel punch handle 17, and also constitutes a portion of a later-described first connection mechanism 46.

Figure 9A:
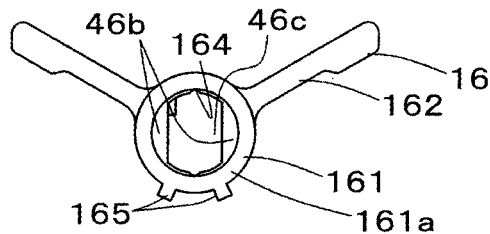
FIG. 9A is a plan view of the keel punch.
Figure 9B:
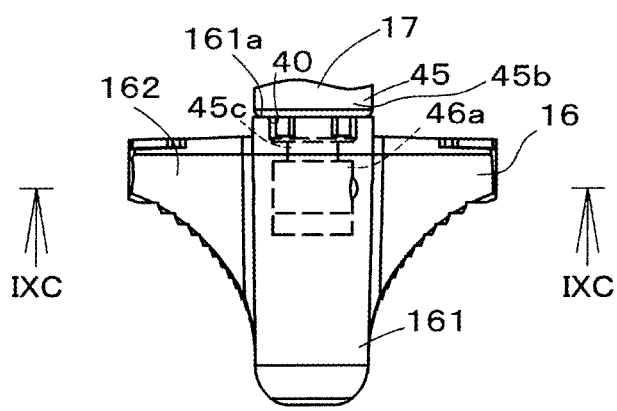
FIG. 9B is a front elevational view of a main portion, showing a state in which the keel punch has been connected to the keel punch handle.
Figure 9C:
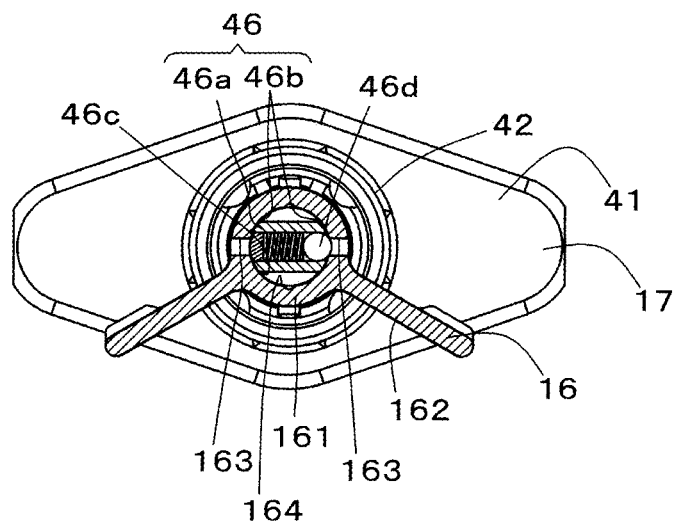
FIG. 9C is a cross-sectional view taken along a line IXC-IXC in FIG. 9B.

Next, a description will be given of a more detailed configuration of the keel punch 16 that is operated by the keel punch handle 17. FIG. 9A is a plan view of the keel punch 16. FIG. 9B is a front elevational view of a main portion, showing a state in which the keel punch 16 has been connected to the keel punch handle 17. FIG. 9C is a cross-sectional view taken along a line IXC-IXC in FIG. 9B. FIG. 10A is a side view of a main portion, showing a state in which the keel punch 16 has been connected to the keel punch handle 17. FIG. 10B is a cross-sectional view taken along a line XB-XB in FIG. 10A.

Referring to FIGS. 7, 9A to 9C, 10A, and 10B, the keel punch 16 is provided to form a hole portion for embedding a stud of a tray (not shown) of the tibial component into the proximal portion 101 of the tibia 100, for example. The keel punch 16 is driven into the proximal portion 101 in which a preparatory hole has been formed by the drill 14. The keel punch 16 is formed into a V-shape when seen in a plan view. The keel punch 16 is formed symmetrically in the internal-external direction X1.

The keel punch 16 has the tubular portion 161 and the pair of wing portions 162.

In this embodiment, the tubular portion 161 is formed into a cylindrical shape, and one end portion thereof is open upward. A portion of the tubular portion 161 on a leading end side is closed. Positioning portions 163 are formed in the tubular portion 161. The positioning portions 163 are provided to define the position of the keel punch handle 17 in the circumferential direction relative to the keel punch 16. A plurality of (in this embodiment, two) positioning portions 163 are provided at equal intervals in the circumferential direction of the tubular portion 161. In this embodiment, the positioning portions 163 are through-holes formed in the tubular portion 161.

The pair of wing portions 162 extends from an outer-circumferential portion of the tubular portion 161. The pair of wing portions 162 is provided as plate-shaped members that have cutters in their lower faces. The wing portions 162 are formed such that the lower faces extend upward as they extend farther from the tubular portion 161, and also extend rearward as they extend farther from the tubular portion 161.

The first connection mechanism 46 is configured to allow the keel punch handle 17 and the keel punch 16, which have the above configuration, to be attached to and detached from each other, and to prevent the keel punch handle 17 from coming out from the keel punch 16. In this embodiment, the first connection mechanism 46 is arranged within the tubular portion 161 of the keel punch 16 when the keel punch 16 is connected to the keel punch handle 17.

The first connection mechanism 46 includes a first protrusion 46a, which is formed in either one of the keel punch handle 17 and the keel punch 16 and serves as a first connecting portion, and first projections 46b, which are formed in the other one of the keel punch handle 17 and the keel punch 16 and serve as a first connected portion.

More specifically, the first protrusion 46a is formed in either one of the insertion end portion 45 and the tubular portion 161, and the first projections 46b that are to be connected to the first protrusion 46a are formed in the other one of the insertion end portion 45 and the tubular portion 161. In this embodiment, the first protrusion 46a is formed in the fourth portion 45d of the insertion end portion 45, and the first projections 46b are formed in the tubular portion 161. Note that the first projections (first connected portion) may be formed in the fourth portion 45d of the insertion end portion 45, and the first protrusion (first connecting portion) may be formed in the tubular portion 161.

The first protrusion 46a is provided as a leading end portion of the keel punch handle 17. In this embodiment, the fourth portion 45d of the insertion end portion 45 is formed by the first protrusion 46a. The first protrusion 46a is arranged within an area surrounded by an outline of the second portion 45b when seen from below. The first protrusion 46a is formed into an elongated rectangular column shape, and has a rectangular outline portion in its cross-section orthogonal to the axial direction of the keel punch handle 17. The first protrusion 46a is arranged coaxially with the first portion 45a to the third portion 45c of the insertion end portion 45. In this embodiment, the first protrusion 46a is formed into an elongated shape with a lengthwise direction being the lengthwise direction of the flat portion 41 (the left-right direction in FIG. 9B), and a widthwise direction being the widthwise direction of the flat portion 41 (the direction orthogonal to the paper plane in FIG. 9B), when seen from the side.

The first projections 46b are formed on an inner-circumferential face 164 of the tubular portion 161, within the tubular portion 161 of the keel punch 16. The first projections 46b protrude inward of the tubular portion 161 from the inner-circumferential face 164 so as to partially block the inner-circumferential face 164, which has a circular shape, of the tubular portion 161, when seen in a plan view. In this embodiment, the first projections 46b are configured to allow the first protrusion 46a to pass between the first projections 46b when the first protrusion 46a is at a predetermined position in the circumferential direction of the keel punch 16, and to restrict the first protrusion 46a from passing between the first projections 46b when the first protrusion 46a is at another position in the circumferential direction.

In this embodiment, the first projections 46b are formed symmetrically with respect to each other when seen in a plan view, and have a shape that includes a portion of a circle. More specifically, one of the first projections 46b has an outline shape demarcated by a line that extends straight to connect two points on the inner-circumferential face 164 when seen in a plan view, and a portion of the inner-circumferential face 164 that is demarcated by this line. The other one of the first projections 46b has a similar shape. Thus, the first projections 46b are provided to form a pair at a pitch of 180 degrees on the inner-circumferential face 164 of the tubular portion 161. According to this configuration, a passage hole portion 46c is formed in the tubular portion 161, the passage hole portion 46c having a cross-sectional shape that matches the cross-sectional shape (elongated rectangular shape) of the first protrusion 46a. The thickness of the first projections 46b (the thickness of the keel punch 16 in the axial direction) is set smaller than the length of the third portion 45c of the insertion end portion 45 of the keel punch handle 17.

Also, the first connection mechanism 46 includes a ball plunger 46d, which serves as a positioning mechanism. The ball plunger 46d is provided to define the position of the keel punch handle 17 in the rotational direction relative to the keel punch 16. The ball plunger 46d has a configuration in which a spring and a ball are accommodated in a space formed in the first protrusion 46a. The ball in the ball plunger 46d is partially exposed in a side face of the first protrusion 46a that has a smaller width. When subjected to an applied pressure, the ball in the ball plunger 46d withdraws into the first protrusion 46a against elastic repulsive force of the spring. The ball in the ball plunger 46d is configured to mate with either one of the positioning portions 163 within the tubular portion 161, and this mating can notify an operator that the keel punch handle 17 has reached a locking position relative to the keel punch 16.

According to the above configuration, when the keel punch handle 17 is connected to the keel punch 16, that is, when the insertion end portion 45 is inserted into the keel punch 16, the first protrusion 46a is inserted into the tubular portion 161 so as to pass between the first projections 46b. Then, the first stopper 40 is received by the opening edge portion 161a of the tubular portion 161. When the first stopper 40 is at the position at which it is received by the opening edge portion 161a, the position of the first protrusion 46a is set on the distal side of the position of the space between the pair of the first projections 46b within the tubular portion 161. The third portion 45c of the insertion end portion 45 is located between the pair of first projections 46b.

In a state in which the insertion end portion 45 has been inserted in the tubular portion 161, the first protrusion 46a is connected to and disconnected from the first projections 46b through relative displacement of the keel punch handle 17 and the keel punch 16. In this embodiment, the aforementioned connection and disconnection are performed by moving the keel punch handle 17 in a predetermined first direction D1, which differs from the axial direction of the keel punch handle 17, relative to the keel punch 16.

The first direction D1 includes a first connecting direction D11 for connecting the keel punch handle 17 to the keel punch 16, and a first disconnecting direction D12 for canceling this connection that is opposite to the first connecting direction D11. In this embodiment, the first direction D1 is a rotational direction around an axis parallel to the axial direction of the keel punch handle 17. Note that the first direction D1 may alternatively be another direction, such as a helical direction around the aforementioned axis.

In this embodiment, the keel punch handle 17 is connected (locked) to the keel punch 16 as a result of the keel punch handle 17 being rotated in the first connecting direction D11 by approximately 90 degrees relative to the keel punch 16, with the insertion end portion 45 inserted in the tubular portion 161. At this time, a portion of the first protrusion 46a faces the pair of first projections 46b in the axial direction. Also, a recession formed in the third portion 45c of the insertion end portion 45 and the first protrusion 46a work together to hold each of the pair of first projections 46b from two opposite sides. As a result, the keel punch handle 17 and the keel punch 16 can be displaced integrally. At this time, the ball in the ball plunger 46d is fitted to one of the positioning portions 163 of the tubular portion 161.

If, in this state, the keel punch handle 17 is rotated by 90 degrees in the first disconnecting direction D12, the ball in the ball plunger 46d rotates so as to come out from the positioning portion 163. Then, the first protrusion 46b assumes an orientation that allows the first protrusion 46a to pass between the pair of projections 46b, and the keel punch handle 17 can be pulled out of the keel punch 16.

Figure 11:
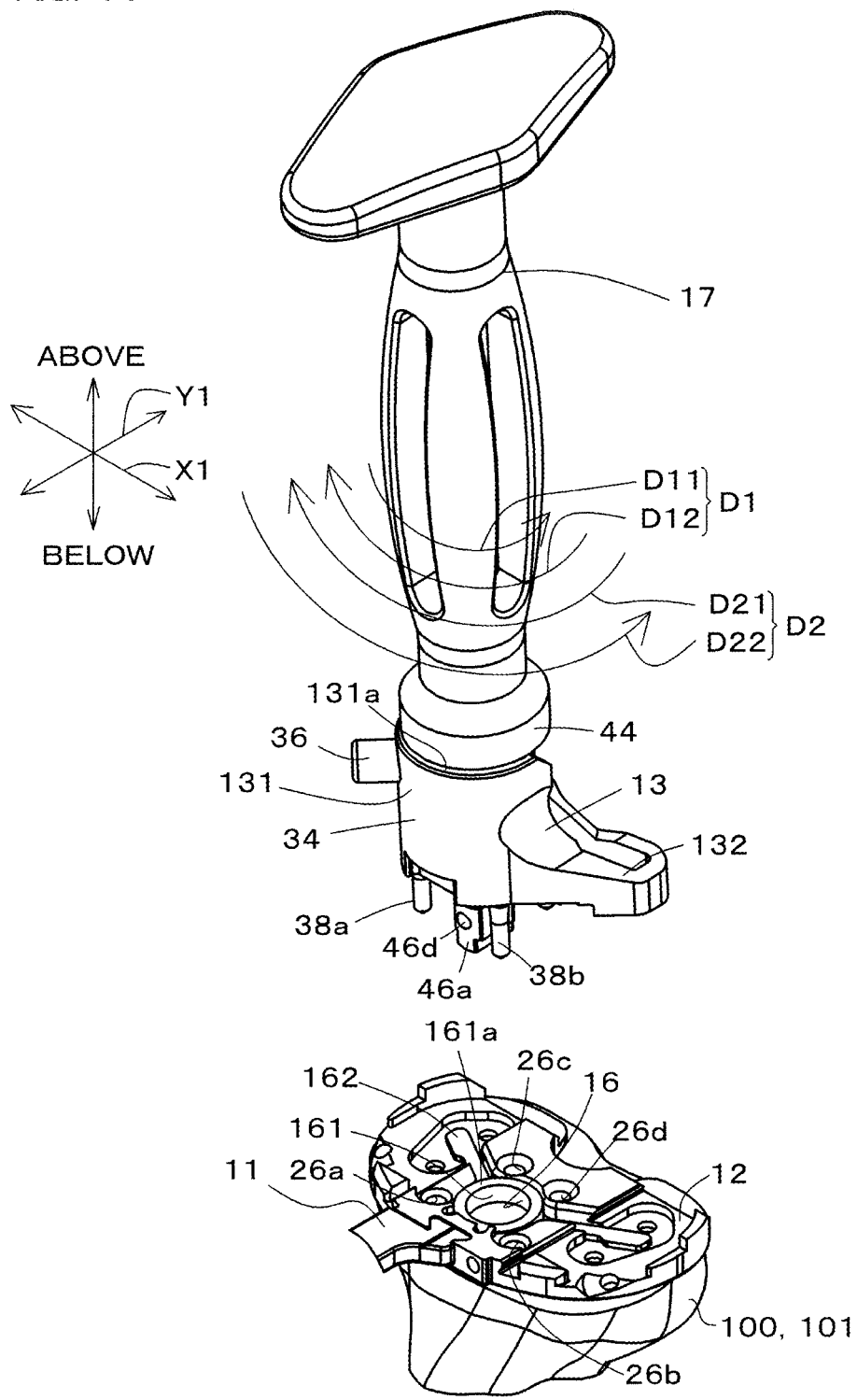
FIG. 11 is a perspective view showing a state in which the keel punch handle has been connected to the keel punch guide.
Figure 12B:
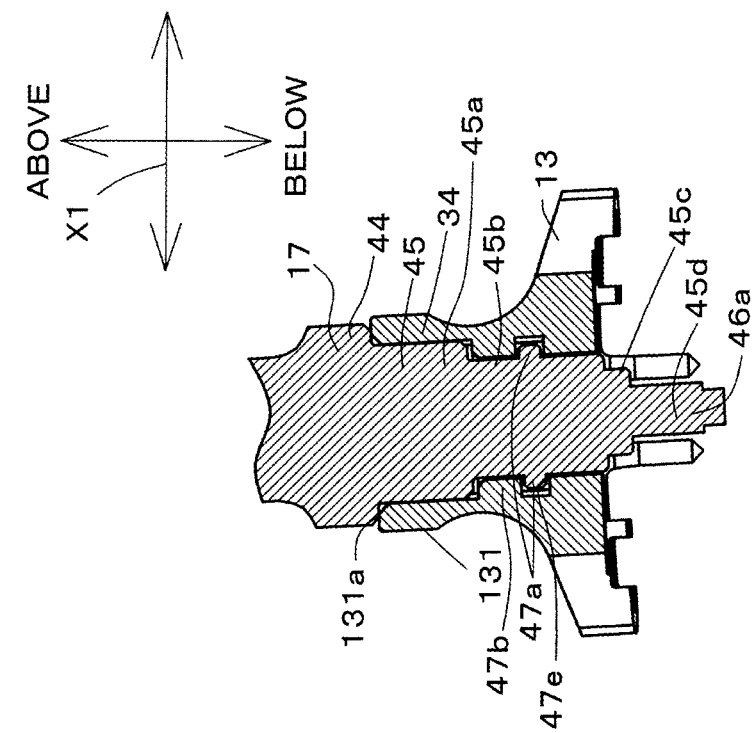
FIG. 12B is a cross-sectional view taken along a line XIIB-XIIB in FIG. 12A.
Figure 12A:
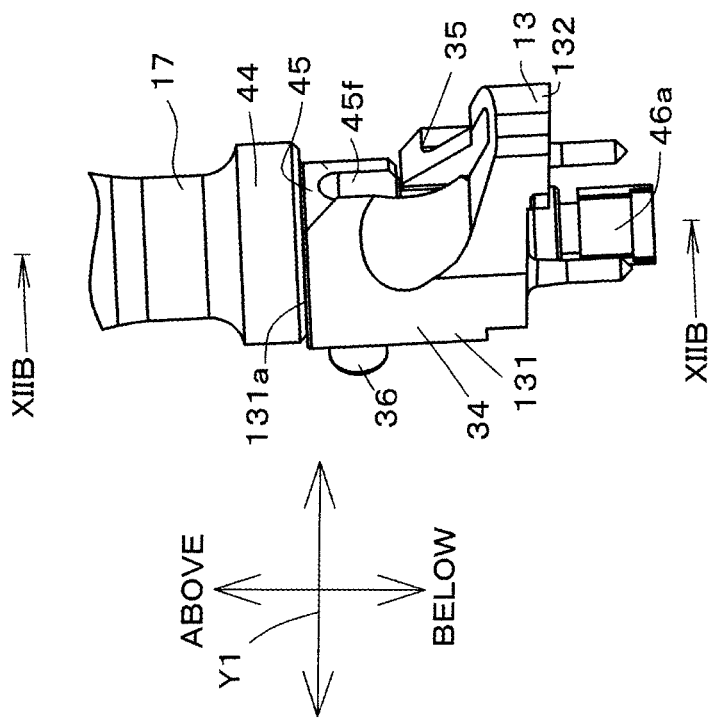
FIG. 12A is a side view showing a state in which the keel punch handle has been connected to the keel punch guide.

FIG. 11 is a perspective view showing a state in which the keel punch handle 17 has been connected to the keel punch guide 13. FIG. 12A is a side view showing a state in which the keel punch handle 17 has been connected to the keel punch guide 13. FIG. 12B is a cross-sectional view taken along a line XIIB-XIIB in FIG. 12A. FIG. 13 is a side view showing a state in which the keel punch handle 17 has been connected to the keel punch 16, together with the keel punch guide 13, and partially shows cross-sections of these components.

Referring to FIGS. 6C, 11, 12A, 12B, and 13, a second connection mechanism 47 is configured to enable the keel punch handle 17 to be attached to and detached from the keel punch guide 13, and to integrally connect the keel punch handle 17 to the keel punch guide 13. In this embodiment, when the keel punch guide 13 is connected to the keel punch handle 17, the second connection mechanism 47 is arranged within the tubular portion 131 of the keel punch guide 13.

The second connection mechanism 47 includes second protrusions 47a, which serve as a second connecting portion formed in either one of the keel punch handle 17 and the keel punch guide 13, and second connected portions 47b and 47c, which are formed in the other one of the keel punch handle 17 and the keel punch guide 13.

More specifically, the second protrusions 47a are formed in either one of the insertion end portion 45 and the tubular portion 131, and the second connected portions 47b and 47c that are to be connected to the second protrusions 47a are formed in the other one of the insertion end portion 45 and the tubular portion 131. In this embodiment, a pair of second protrusions 47a is formed in the second portion 45b of the insertion end portion 45, and the second connected portions 47b and 47c are formed in the tubular portion 131. Note that the number of second protrusions 47a and the number of second connected portions 47b and 47c may be one. A configuration may alternatively be employed in which the second connected portions are formed in the second portion 45b of the insertion end portion 45, and the second protrusions (second connecting portions) are formed in the tubular portion 131.

The second protrusions 47a are small piece portions that are formed on an outer-circumferential face of the second portion 45b of the insertion end portion 45 and protrude radially outward from the second portion 45b. The second protrusions 47a are arranged at an even pitch of 180 degrees in the circumferential direction of the keel punch handle 17. The second protrusions 47a are aligned with each other at positions distant, on the second stopper 44 side, from the first protrusion 46a in the axial direction of the keel punch handle 17. The second protrusions 47a extend in the widthwise direction of the first protrusion 46a (the left-right direction in FIG. 13). When the keel punch handle 17 is connected to the keel punch 16 (i.e. at the time shown in FIG. 13), the second protrusions 47a are located outside of the keel punch 16.

The second connected portions 47b and 47c are formed on an inner-circumferential face of the tubular portion 131 of the keel punch guide 13. The second connected portion 47b is arranged in the high-wall portion 34 of the tubular portion 131, and the second connected portion 47c is arranged in the low-wall portion 35 of the tubular portion 131.

The second connected portion 47b is arranged on the lower side of the inner-circumferential face of the high-wall portion 34, and is formed into a shape protruding radially inward from this inner-circumferential face. The second connected portion 47c is arranged over the substantially entire area of an inner-circumferential face of the low-wall portion 35, and is formed into a shape protruding radially inward from this inner-circumferential face. In this embodiment, the height (the length in the axial direction) of the second connected portion 47b and the height (the length in the axial direction) of the second connected portion 47c are set to substantially the same length. The second connected portions 47b and 47c are formed substantially symmetrically in the front-rear direction Y1.

The second connected portion 47b includes a vertical groove portion 47d and a lateral groove portion 47e. The second connected portion 47c includes a vertical groove portion 47f and a lateral groove portion 47g.

The vertical groove portions 47d and 47f are groove portions that extend in the axial direction of the tubular portion 131, and have shapes that are open in the axial direction of the tubular portion 131 and radially inward. The groove width of the vertical groove portions 47d and 47f (the length of the tubular portion 131 in the circumferential direction) is set such that the corresponding second protrusions 47a can pass therethrough. The groove width of the vertical groove portion 47d (see FIG. 6C) is set such that projections 165 formed on the opening end side of the keel punch 16 can pass therethrough. The vertical groove portions 47d and 47f are provided as portions through which the second protrusions 47a can pass therethrough in the axial direction of the tubular portion 131. The arrangement pitch of the vertical groove portions 47d and 47f in the circumferential direction of the tubular portion 131 are set to be the same as the arrangement pitch of the second protrusions 47a in the circumferential direction of the keel punch handle 17. In this embodiment, the vertical groove portions 47d and 47f are arranged in a front end portion and a rear end portion, respectively, of the inner-circumferential face of the tubular portion 131. The lateral groove portion 47e is formed to as to intersect the vertical groove portion 47d, and the lateral groove portion 47g is formed so as to intersect the vertical groove portion 47f.

The lateral groove portions 47e and 47g are provided to be mated with the corresponding second protrusions 47a, thereby integrally connecting the keel punch handle 17 to the keel punch guide 13. The lateral groove portions 47e and 47g are groove portions that extend in the circumferential direction of the tubular portion 131, and extend so as to intersect (in this embodiment, so as to be orthogonal to) the corresponding vertical groove portions 47d and 47f. Thus, the lateral groove portions 47e and 47g span both sides of the corresponding vertical groove portions 47d and 47f in the circumferential direction. In this embodiment, the lateral groove portions 47e and 47g are formed over the entire area of the corresponding high-wall portion 34 and low-wall portion 35 in the circumferential direction.

The distance in the axial direction of the keel punch guide 13 from the opening edge portion 131a of the tubular portion 131 to the lateral groove portions 47e and 47g is set to be substantially the same as the distance in the axial direction of the keel punch handle 17 from the second stopper 44 to the second protrusions 47a.

According to the above configuration, when the keel punch handle 17 is connected to the keel punch guide 13, that is, when the insertion end portion 45 is inserted into the keel punch guide 13, the second protrusions 47a pass through the corresponding vertical groove portions 47d and 47f. Then, the second stopper 44 is received by the opening edge portion 131a of the tubular portion 131. When the second stopper 44 is received by the opening edge portion 131a, the second protrusions 47a can enter and exit from the corresponding lateral groove portions 47e and 47g.

In a state in which the insertion end portion 45 has been inserted in the tubular portion 131, the second protrusions 47a are connected to and disconnected from the corresponding lateral groove portions 47e and 47g of the second connected portions 47b and 47c through relative displacement of the keel punch handle 17 and the keel punch guide 13. In this embodiment, the aforementioned connection and disconnection are performed by moving the keel punch handle 17 in a predetermined second direction D2, which differs from the axial direction of the keel punch handle 17, relative to the keel punch guide 13.

The second direction D2 includes a second connecting direction D21 for connecting the keel punch handle 17 to the keel punch guide 13, and a second disconnecting direction D22 for canceling this connection that is opposite to the second connecting direction D21. In this embodiment, the second direction D2 is a rotational direction around an axis parallel to the axial direction of the keel punch handle 17. Note that the second direction may alternatively be another direction, such as a helical direction around the aforementioned axis.

In this embodiment, the keel punch handle 17 is connected (locked) to the keel punch guide 13 as a result of the keel punch handle 17 being rotated in the second connecting direction D21 by approximately 90 degrees relative to the keel punch guide 13, with the insertion end portion 45 inserted in the tubular portion 131. At this time, the second protrusions 47a enter the corresponding lateral groove portions 47e and 47g from the corresponding vertical groove portions 47d and 47f. As a result, the second protrusions 47a are fitted into the corresponding lateral groove portions 47e and 47g, and enter a state of being held from above and below by the lateral groove portions 47e and 47g, respectively. Furthermore, as a result of the ball in the ball plunger 36 in the keel punch guide 13 being received by the connected portion 45f of the keel punch handle 17, the keel punch handle 17 is positioned in the circumferential direction relative to the keel punch guide 13. As a result, the keel punch handle 17 and the keel punch guide 13 can be displaced integrally.

If, in this state, the keel punch handle 17 is rotated by 90 degrees in the second disconnecting direction D22, the keel punch handle 17 rotates such that the ball in the ball plunger 36 comes out from the connected portion 45f. Also, the second protrusions 47a return to the corresponding vertical groove portions 47d and 47f. Thus, the keel punch handle 17 can be pulled out of the keel punch guide 13.

In this embodiment, the first disconnecting direction D12 and the second connecting direction D21 are the same direction. With this configuration, it is possible to simultaneously cancel the connection between the keel punch handle 17 and the keel punch 16 through the first connection mechanism 46 and connect the keel punch handle 17 to the keel punch guide 13 through the second connection mechanism 47, by displacing the keel punch handle 17 in one direction relative to the keel punch 16 and the keel punch guide 13.

The first connecting direction D11 is opposite to the second connecting direction D21. That is to say, the direction (the first connecting direction D11) in which the keel punch handle 17 is displaced relative to the keel punch 16 in order to connect the keel punch handle 17 to the keel punch 16 through the first connection mechanism 46 is set to be opposite to the direction (the second connecting direction D21) in which the keel punch handle 17 is displaced relative to the keel punch guide 13 in order to connect the keel punch handle 17 to the keel punch guide 13 through the second connection mechanism 47.

Figure 15A:
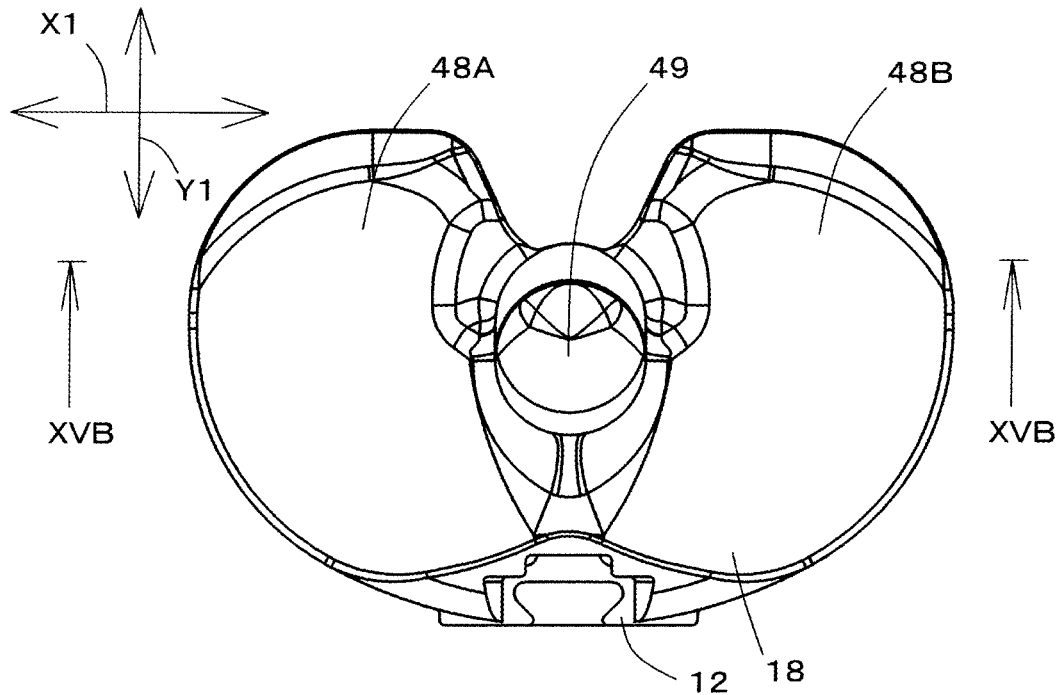
FIG. 15A is a plan view of the template and the tibial insert trial.
Figure 15B:
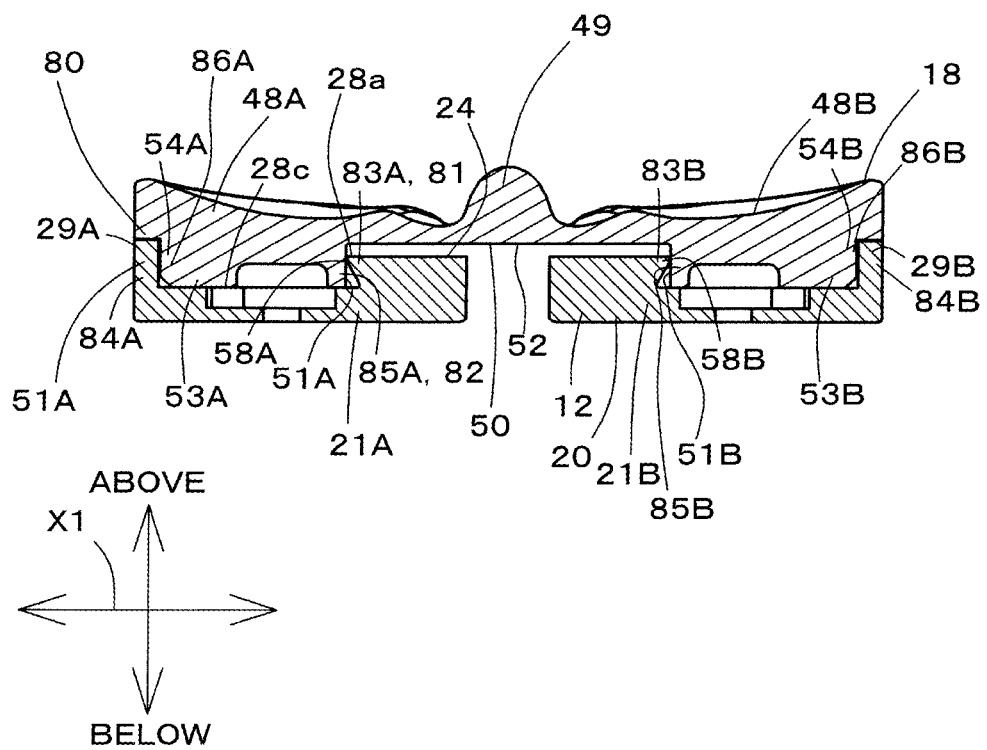
FIG. 15B is a cross-sectional view taken along a line XVB-XVB in FIG. 15A.
Figure 16:
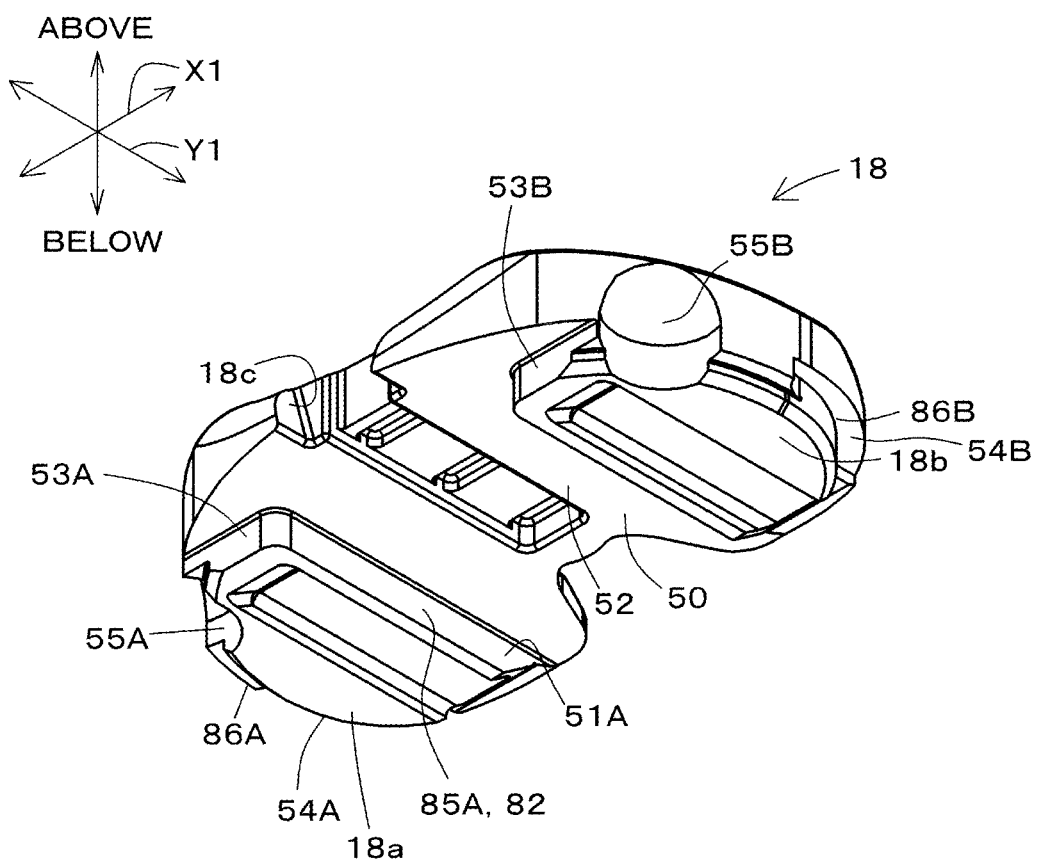
FIG. 16 is a perspective view of the tibial insert trial.

FIG. 14A is a perspective view showing a state in which the template 12 is attached to the proximal portion 101 of the tibia 100, before the tibial insert trial 18 is attached to the template 12. FIG. 14B is a perspective view showing a state in which the template 12 has been attached to the proximal portion 101 of the tibia 100, and the tibial insert trial 18 has been attached to the template 12. FIG. 15A is a plan view of the template 12 and the tibial insert trial 18. FIG. 15B is a cross-sectional view taken along a line XVB-XVB in FIG. 15A. FIG. 16 is a perspective view of the tibial insert trial 18.

Referring to FIGS. 14A and 14B, 15A and 15B, and 16, the tibial insert trial 18 is a member that is to be temporarily attached to the proximal portion 101 of the tibia 100 when a tibial component (not shown) is selected. The tibial insert trial 18 is formed into a shape with a rear end portion of a central portion in the inward-outward direction X1 being recessed forward.

The tibial insert trial 18 has a pair of tibial joint surfaces 48A and 48B, which are arranged in the inward-outward direction X1, a post 49, which is arranged between these tibial joint surfaces 48A and 48B, and a bottom portion 50.

In this embodiment, a plurality of tibial insert trials 18 with different shapes of the tibial joint surfaces 48A and 48B and different shapes of the post 49 are provided. A tibial insert trial 18 will be described as an example. Note that other tibial insert trials have the same configuration except that the shape of the tibial joint surfaces and the shape of the post differ.

The two tibial joint surfaces 48A and 48B are portions that mimic tibial joint surfaces of a tibial component, and have a recessed shape similar to that of the tibial joint surfaces of the tibial component. The pair of tibial joint surfaces 48A and 48B and the post 49 face upward. The post 49 is a portion that mimics a post of a tibial component, and has a columnar shape similar to that of the post of the tibial component.

The bottom portion 50 has second rails 51A and 51B, and a second spacer receiving portion 52.

The second rails 51A and 51B are formed in a pair of protrusions 53A and 53B that protrude downward from the bottom portion 50. The two protrusions 53A and 53B are spaced apart in the inward-outward direction X1, and are formed into tab shapes extending straight in the front-rear direction Y1. The second rails 51A and 51B are formed in an inner face of the pair of protrusions 53A and 53B, respectively, in the inward-outward direction X1, and extend straight in the front-rear direction Y1. Assuming that the central portion 20 of the template 12 is a first rail, the second rails 51A and 51B are arranged so as to sandwich the central portion 20. With this configuration, the tibial insert trial 18 can slide in the front-rear direction Y1 on the template 12, with the second rails 51A and 51B sandwiching the central portion 20 (the first rail).

When the spacer 19 is not inserted between the template 12 and the tibial insert trial 18, the pair of protrusions 53A and 53B are received by the third upper face 28c of the template 12. At this time, a gap is formed between the first spacer receiving portion 24 and the second spacer receiving portion 52.

The pair of protrusions 53A and 53B is arranged between the central portion 20 and corresponding side end walls 29A and 29B of the template 12, and is sandwiched between the central portion 20 and the corresponding side end walls 29A and 29B. Side end wall receiving portions 54A and 54B are formed in a rear portion of an end portion, in the inward-outward direction X1, of the bottom portion 50 of the tibial insert trial 18. These side end wall receiving portions 54A and 54B are cutout portions configured to be placed on the corresponding side end walls 29A and 29B of the template 12, and extend forward and rearward.

Intermediate portions of the side end wall receiving portions 54A and 54B each have a step portion, and the height position of rear portions of the side end wall receiving portions 54A and 54B is set higher than the height position of front portions of the side end wall receiving portions 54A and 54B. The side end wall receiving portions 54A and 54B are arranged to face the corresponding side end walls 29A and 29B, and can be received by the side end walls 29A and 29B, respectively. Recessions 55A and 55B are formed on the front side of the side end wall receiving portions 54A and 54B of the tibial insert trial 18. When the tibial insert trial 18 is placed on the template 12, the recessions 55A and 55B are configured to expose the fixing pin insertion hole portions 30a and 30b, which are arranged at a front end of the template 12, upward and forward.

In a state in which the tibial insert trial 18 has been placed on the template 12, a central portion, in the inward-outward direction X1, of the bottom portion 50 of the tibial insert trial 18 faces the first upper face 28a of the template 12 in the up-down direction, and a flat face formed in the central portion of the bottom portion 50 includes the second spacer receiving portion 52 for receiving the spacer 19. The second spacer receiving portion 52 is a portion that has a substantially T-shape when seen from below, and having a portion that extends in the front-rear direction Y1 and is formed between the pair of protrusions 53A and 53B, and a portion arranged forward of the pair of protrusions 53A and 53B.

In a state in which the tibial insert trial 18 has been placed on the template 12, the second spacer receiving portion 52 is substantially parallel to the first spacer receiving portion 24 of the template 12. When the tibial insert trial 18 has been placed on the template 12, an insertion space 57, into which the spacer is to be inserted, is formed between the template 12 and the tibial insert trial 18. The insertion space 57 is formed by the spacer receiving portions 24 and 52, the central portion 20 (the first rail), and the second rails 51A and 51B. In the inward-outward direction X1, the length of the insertion space 57 is set larger than the length of a later-described body portion 61 of the spacer 19.

Figure 17A:
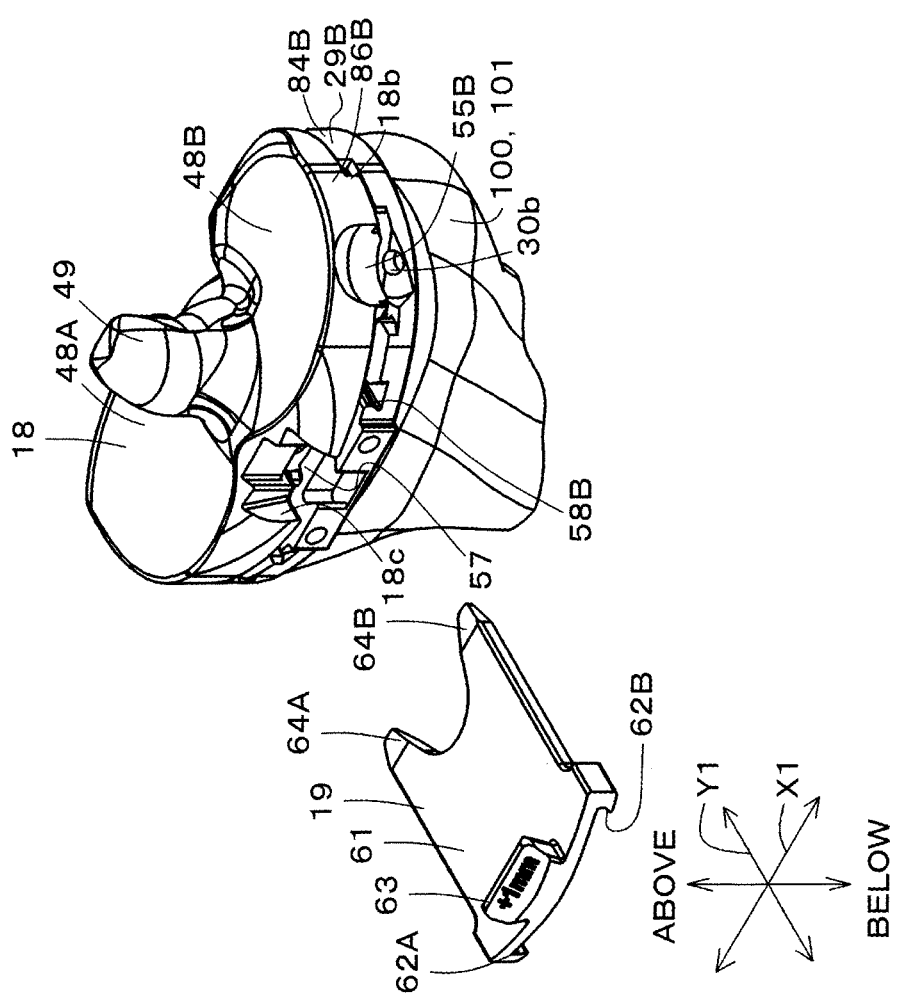
FIG. 17A is a perspective view showing the template and the tibial insert trial before a spacer is attached thereto.
Figure 17B:
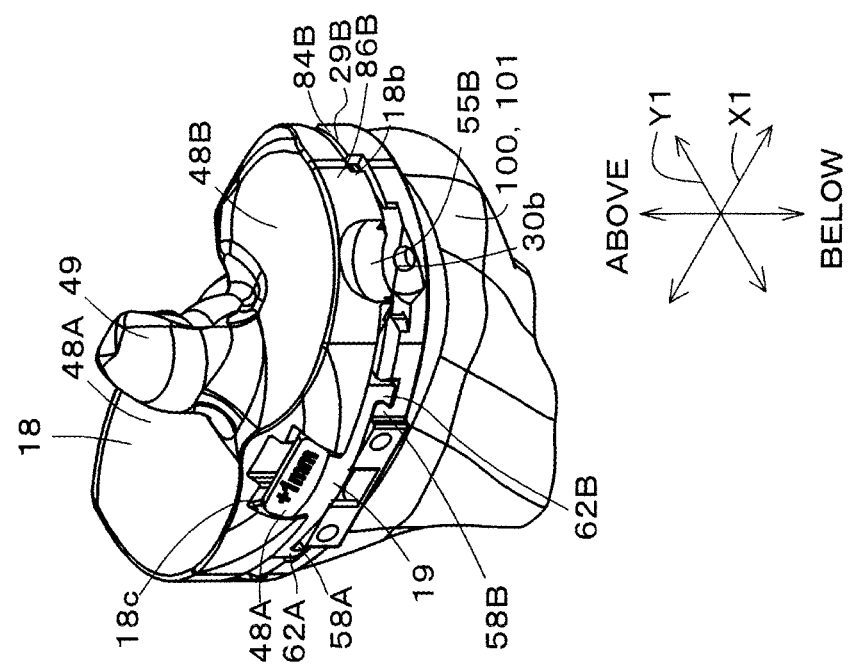
FIG. 17B is a perspective view showing the template and the tibial insert trial to which the spacer has been attached.
Figure 18A:
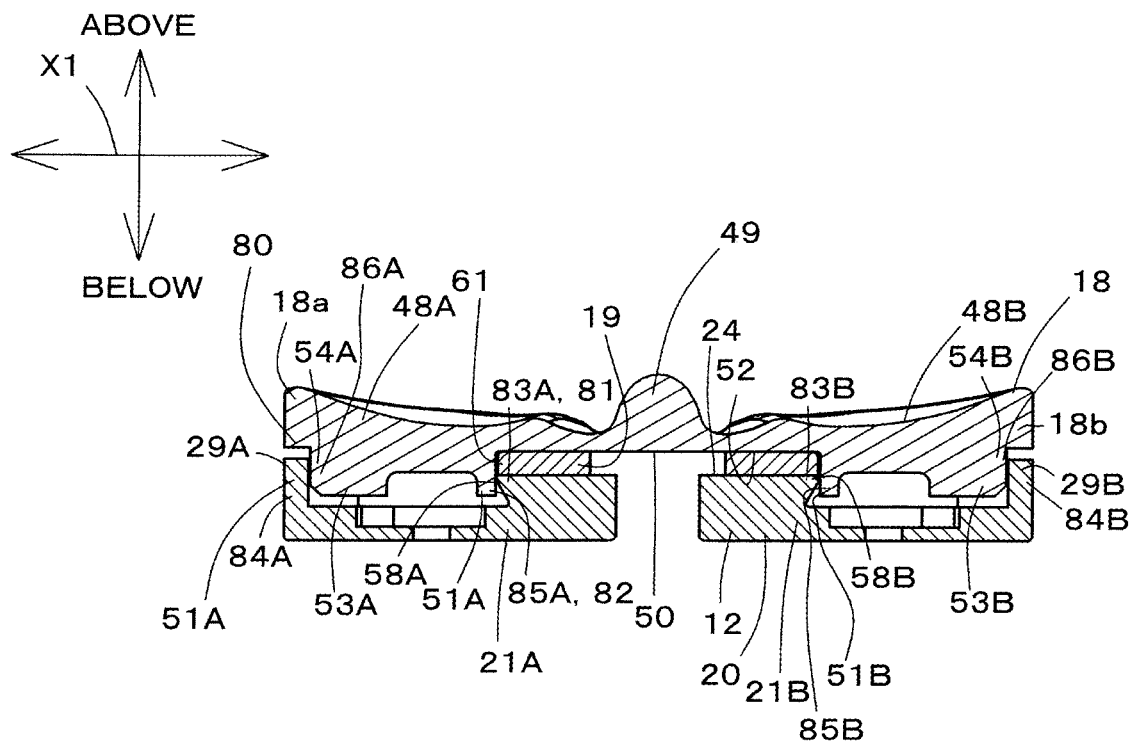
FIG. 18A is a cross-sectional view showing a state in which the spacer is arranged between the template and the tibial insert trial, and shows a cross-section along a section corresponding to the line XVB-XVB in FIG. 15A.
Figure 18B:
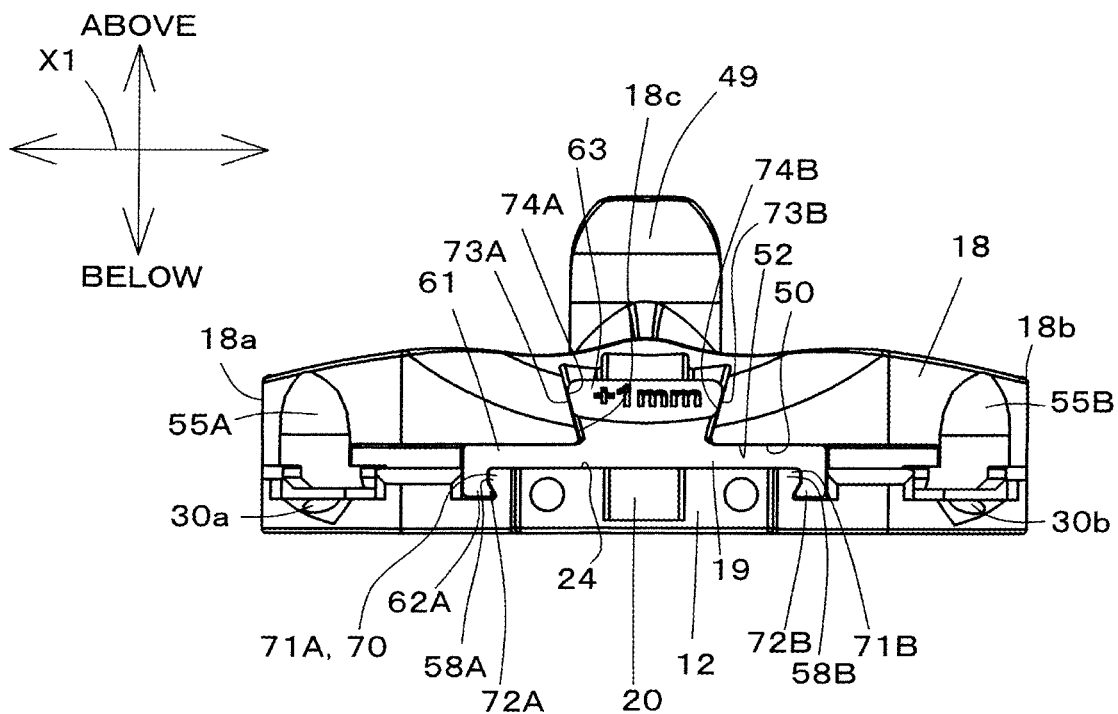
FIG. 18B is a front elevational view showing a state in which the spacer is arranged between the template and the tibial insert trial.

FIG. 17A is a perspective view showing the template 12 and the tibial insert trial 18 before the spacer 19 is attached thereto. FIG. 17B is a perspective view showing the template 12 and the tibial insert trial 18 to which the spacer 19 has been attached. FIG. 18A is a cross-sectional view showing a state in which the spacer 19 is arranged between the template 12 and the tibial insert trial 18, and shows a cross-section taken along a section corresponding to a line XVB-XVB in FIG. 15A. FIG. 18B is a front elevational view showing a state in which the spacer 19 is arranged between the template 12 and the tibial insert trial 18.

Referring to FIGS. 17A and 17B, and 18A and 18B, the spacer 19 is provided to adjust the height position of the tibial insert trial 18 relative to the template 12. Although a plurality of spacers with different thicknesses of the body portion are provided in this embodiment, the spacer 19 will be described as an example. Note that other spacers have the same configuration except that the thickness of the body portion differs from that of the spacer 19.

The spacer 19 is configured to be arranged in a partial area of the template 12 in the inward-outward direction X1 of a patient and in the central portion 20 of the template 12, and inserted between the template 12 and the tibial insert trial 18. Constituents of the spacer 19 other than a display portion of a later-described stopper 63 are formed symmetrically in the inward-outward direction X1.

The spacer 19 includes the body portion 61, which is formed into a flat plate shape, and guide portions 62A and 62B and a stopper 63, which are formed in a base end portion of the body portion 61.

The body portion 61 is formed into a flat plate shape having a predetermined thickness, and extends in the front-rear direction Y1. The thickness of the body portion 61 is fixed, except in a leading end portion. The length of the body portion 61 in the inward-outward direction X1 is set smaller than the length of the first spacer receiving portion 24. A leading end of a central portion of the body portion 61 in the inward-outward direction X1 has a shape that is recessed forward. Leading ends at both ends of the body portion 61 in the inward-outward direction are formed by tapered portions 64A and 64B. The tapered portions 64A and 64B are leading end portions of the spacer 19 in the inserting direction in which the spacer 19 is inserted into the insertion space 57 between the template 12 and the tibial insert trial 18.

The tapered portions 64A and 64B are formed into shapes that are tapered and decrease in thickness toward the leading end of the spacer 19. In the inward-outward direction X1, the length of the spacer insertion space 57 is set larger than the length of the body portion 61 of the spacer 19. When the spacer 19 is inserted into the insertion space 57, the tapered portions 64A and 64B are first inserted into the insertion space 57. Then, the gap between the first spacer receiving portion 24 (the first upper face 28a) of the template 12 and the second spacer receiving portion 52 of the tibial insert trial 18 is expanded by the tapered portions 64A and 64B, and then, a majority of the body portion 61 of the spacer 19 is inserted into the insertion space 57.

During this inserting operation, the guide portions 62A and 62B are configured to respectively slidably mate with the rails 58A and 58B formed in the central portion 20 of the template 12. The rails 58A and 58B are formed in portions in which the template 12 and the tibial insert trial 18 face each other. In this embodiment, the rails 58A and 58B that extend in the front-rear direction Y1 are formed in the two end portions, in the inward-outward direction X1, of a front end portion of the central portion 20 of the template 12. The rails 58A and 58B are formed into inclined shapes that extend outward in the inward-outward direction X1 as they extend upward (from the third upper face 28c toward the first upper face 28a). The rails 58A and 58B form a reverse tapered shape as a whole when seen from the front, and the gap therebetween expands upward. Note that, the rails 58A and 58B are not formed in the portions of the central portion 20 of the template 12 other than the front end portion thereof, as shown in FIG. 3.

The guide portions 62A and 62B of the spacer 19 are formed into hook-shaped portions that are formed in an outer end portion, in the inward-outward direction X1, of the base end portion of the body portion 61. The guide portions 62A and 62B extend downward from the body portion 61, and form a reverse tapered shape such that the gap therebetween narrows downward. After a portion of the spacer 19 has been inserted into the insertion space 57, the guide portions 62A and 62B slidably mate with the corresponding rails 58A and 58B. If, in this state, the spacer 19 is further inserted into the insertion space 57, the stopper 63 is received by a cutout portion 18c of the tibial insert trial 18. Thus, insertion of the space 19 into the insertion space 57 is complete.

The stopper 63 is arranged in the center, in the inward-outward direction X1, of the base end portion of the body portion 61. The stopper 63 is formed into a block shape. A display portion is formed in a front face of the stopper 63, the display portion displaying, by means of a mark or the like, the amount of change in the total thickness of the template 12 and the tibial insert trial 18 when the spacer 19 is inserted in the insertion space 57. For example, if "+1 mm" is displayed on the display portion, the thickness of the body portion 61 of the spacer 19 is thicker, by 1 mm, than the thickness of the insertion space 57 in a state in which the spacer 19 is not inserted therein. In this case, if the spacer 19 is inserted into the insertion space 57, the total thickness of the template 12 and the tibial insert trial 18 increases by 1 mm. The stopper 63 is fitted to the cutout portion 18c formed in the front end portion of the tibial insert trial 18. The cutout portion 18c is a cutout portion that is open forward and upward. As a result of the cutout portion 18c receiving the stopper 63, the spacer 19 is restricted from being further inserted into the insertion space 57.

A tilt restriction mechanism 70 is formed in a state in which the tibial insert trial 18 has been placed on the template 12 and the spacer 19 has been inserted in the insertion space 57. The tilt restriction mechanism 70 is provided to restrict tilting of the tibial insert trial 18 relative to the template 12 around an axis of the tibia 100 that extends in the front-rear direction Y1. In this embodiment, the tilt restriction mechanism 70 is formed in front portions of the template 12, the spacer 19, and the tibial insert trial 18.

Referring to FIG. 18B, the tilt restriction mechanism 70 includes first tilt restriction portions 71A and 71B, which are formed on the upper face side of the template 12, second tilt restriction portions 72A and 72B, which are formed on the lower face side of the spacer 19 and can mate with the first tilt restriction portions 71A and 71B respectively, third tilt restriction portions 73A and 73B, which are formed on the upper face side of the spacer 19, and fourth tilt restriction portions 74A and 74B, which are formed in the tibial insert trial 18 and can mate with the third tilt restriction portions 73A and 73B, respectively.

The first tilt restriction portions 71A and 71B are formed by the aforementioned rails 58A and 58B, respectively. The second tilt restricting portions 72A and 72B are formed by the aforementioned guide portions 62A and 62B. Thus, the first tilt restriction portions 71A and 71B and the second tilt restriction portions 72A and 72B also serve as a rail mechanism. The shapes of the first tilt restriction portions 71A and 71B are formed so as to match the shapes of the second tilt restriction portions 72A and 72B, when seen from the front.

The third tilt restriction portions 73A and 73B are formed in respective end portions, in the inward-outward direction X1, of the stopper 63 at a base end (front end) of the spacer 19. The third tilt restriction portions 73A and 73B extend in the front-rear direction Y1, and are formed into inclined shapes that extend outward in the inward-outward direction X1 as they extend upward from the body portion 61. When seen from the front, the third tilt restriction portions 73A and 73B form a reverse tapered shape as a whole, and the gap therebetween expands as they extend upward.

The fourth tilt restriction portions 74A and 74B are formed at respective end portions, in the inward-outward direction X1, of the cutout portion 18c of tibial insert trial 18. The fourth tilt restriction portions 74A and 74B extend in the front-rear direction Y1, and are formed into inclined shapes that extend outward in the inward-outward direction X1 as they extend upward. When seen from the front, the fourth tilt restriction portions 74A and 74B form a reverse tapered shape as a whole, and the gap therebetween expands as they extend upward. When seen from the front, the shapes of the third tilt restriction portions 73A and 73B are formed so as to match the shapes of the fourth tilt restriction portions 74A and 74B, respectively. Thus, the third tilt restriction portions 73A and 73B and the fourth tilt restriction portions 74A and 74B also serve as a stopper mechanism for preventing the spacer 19 from excessively entering the insertion space 57.

Referring to FIGS. 17B and 18A, a position shift restriction mechanism 80 is provided to restrict a position shift of the tibial insert trial 18 in the inward-outward direction X1 relative to the template 12, in a state in which the tibial insert trial 18 has been placed on the template 12.

The position shift restriction mechanism 80 has a first shift restriction portion 81, which is formed in the template 12, and a second shift restriction portion 82, which is formed in the tibial insert trial 18 and faces the first shift restriction portion 81 in the inward-outward direction X1.

The first shift restriction portion 81 includes first inner shift restriction portions 83A and 83B, which are formed at respective end portions, in the inward-outward direction X1, of the central portion 20 of the template 12, and first outer shift restriction portions 84A and 84B, which are formed in side end walls 29A and 29B, respectively, of the template 12.

The second shift restriction portion 82 includes second inner shift restriction portions 85A and 85B, which are formed by portions of the pair of protrusions 53A and 53B of the tibial insert trial 18, the portions forming the second rails 51A and 51B, and second outer shift restriction portions 86A and 86B, which are formed in end walls 18a and 18b of the tibial insert trial 18. The height of the second inner shift restriction portions 85A and 85B from the bottom portion 50 of the tibial insert trial 18 is set larger than the thickness of the spacer 19. Thus, even when the spacer 19 has been inserted in the insertion space 57, the second inner shift restriction portions 85A and 85B sandwich the first inner shift restriction portions 83A and 83B in the inward-outward direction X1.

The length over which the first outer shift restriction portions 84A and 84B face the second outer shift restriction portions 86A and 86B in the up-down direction is set larger than the thickness of the spacer 19. Thus, even when the spacer 19 has been inserted in the insertion space 57, the first outer shift restriction portions 84A and 84B sandwich the second outer shift restriction portions 86A and 86B in the inward-outward direction X1. The second outer shift restriction portions 86A and 86B are sandwiched by the first outer shift restriction portions 84A and 84B in the inward-outward direction X1. According to the above configuration, the tibial insert trial 18 is restricted from being displaced in the inward-outward direction X1 relative to the template 12 by the contact between the first inner shift restriction portions 83A and 83B and the corresponding second inner shift restriction portions 85A and 85B, or the contact between the first outer shift restriction portions 84A and 84B and the corresponding second outer shift restriction portions 86A and 86B.

Figure 19:
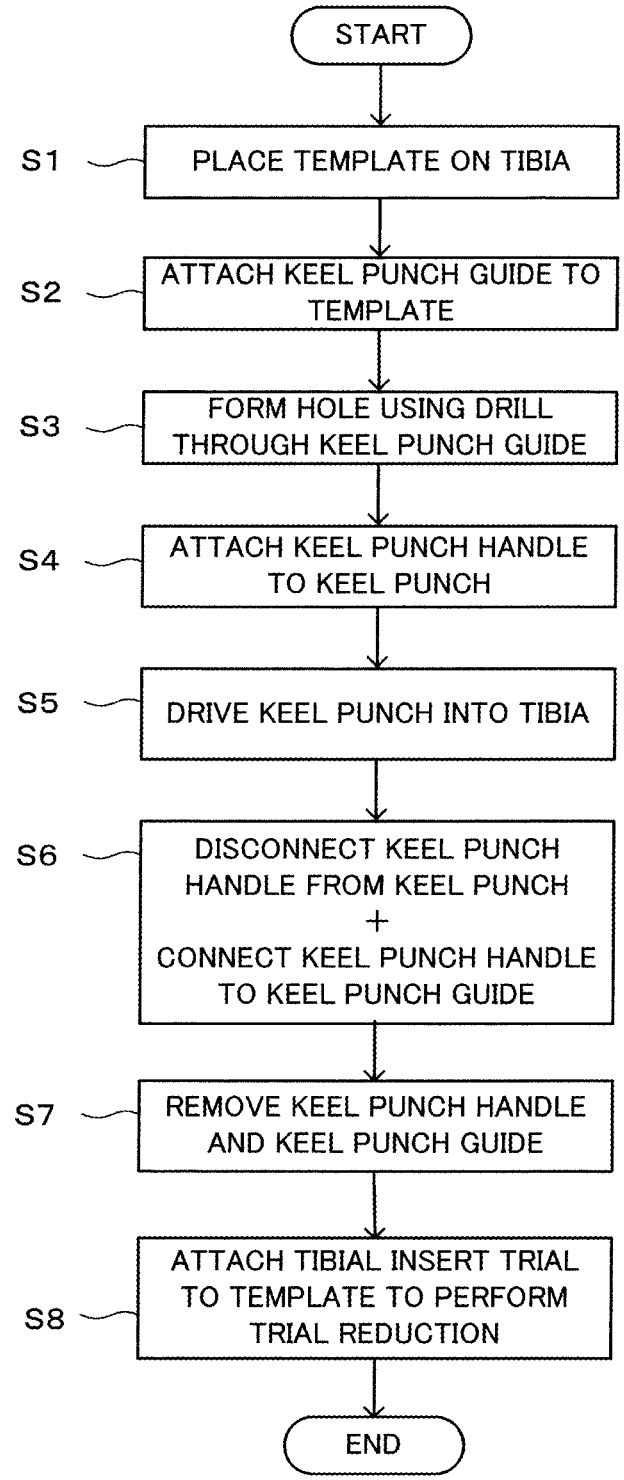
FIG. 19 is a flowchart showing an example of a procedure of an operation performed using a tibial trial attachment instrument assembly.

A schematic configuration of the tibial trial attachment instrument assembly 2 is as described above. Next, main points of a procedure of an operation performed using the tibial trial attachment instrument assembly 2 will be described. FIG. 19 is a flowchart showing an example of a procedure of an operation performed using a tibial trial attachment instrument assembly 2. Note that, when a description is given with reference to the flowchart, diagrams other than the flowchart will also be referenced as appropriate.

When the tibial trial attachment instrument assembly 2 is used, an operator first puts the template 12 onto the cut bone surface 102 of the patient's tibia 100 using the template handle 11, as shown in FIG. 2 (step S1). Next, the operator fixes the studs 38a to 38d of the keel punch guide 13 to the tibia 100 through the corresponding stud insertion hole portions 27a to 27d (step S2). At this time, the operator may fix the template 12 to the tibia 100 using fixing pins (not shown).

Figure 20A:
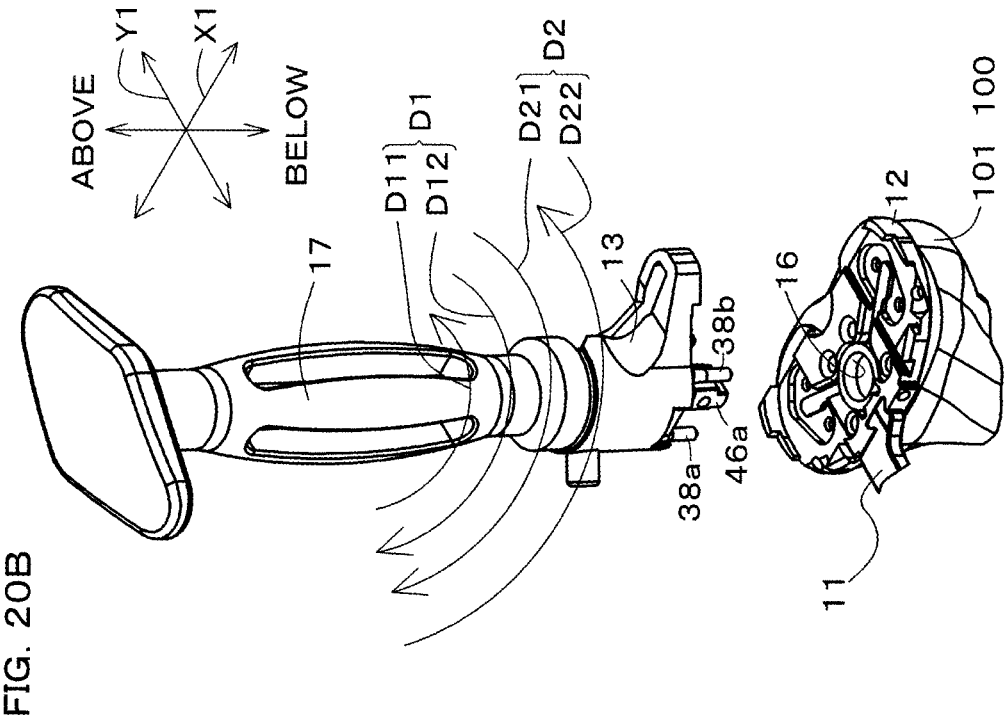
FIGS. 20A and 20B are perspective views for describing an example of an operation performed using the tibial trial attachment instrument.

Referring to FIG. 5, next, the operator inserts, into the keel punch guide 13, the drill 14 to which the stopper 15 has been attached, and forms a preparatory hole in the proximal portion 101 of the tibia 100 (step S3). Next, referring to FIGS. 7 and 20A, the operator connects the keel punch handle 17 to the keel punch 16 by rotating the keel punch handle 17 by 90 degrees in the first connecting direction D11 relative to the keel punch 16 (step S4), and then, the operator drives the keel punch 16 into the proximal portion 101 of the tibia 100 using the keel punch handle 17 and the keel punch guide 13 (step S5).

Figure 20B:
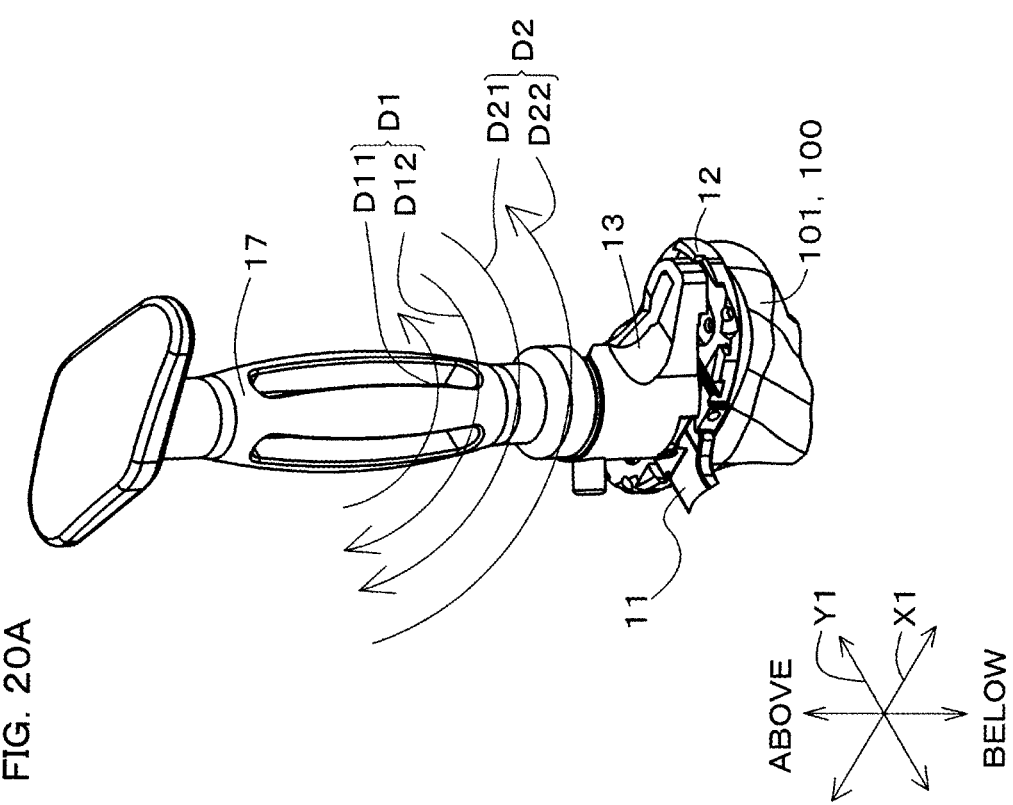

Next, by rotating the keel punch handle 17 by 90 degrees in the first disconnecting direction D12, i.e. the second connecting direction D21, the operator cancels connection between the keel punch handle 17 and the keel punch 16 through the first connection mechanism 46, and connects the keel punch handle 17 to the keel punch guide 13 through the second connection mechanism 47, as shown in FIG. 20B (step S6). In this state, the operator removes the keel punch handle 17 and the keel punch guide 13 from the tibia 100 (step S7).

Referring to FIGS. 17A and 17B, next, the operator attaches the tibial insert trial 18 onto the template 12 to perform a trial reduction (step S8). At this time, if tension of a patient's ligament is weak, the spacer 19 is inserted between the template 12 and the tibial insert trial 18. When the spacer 19 is not inserted between the template 12 and the tibial insert trial 18, a removal tool (not shown) is inserted between the template 12 and the tibial insert trial 18.

As described above, according to the present embodiment, the template 12, the keel punch guide 13, the keel punch 16, the keel punch handle 17, and the tibial insert trial 18 are prepared as a single assembly. Accordingly, these instruments can be prepared collectively, which is less laborious than in the case of preparing these instruments separately. Accordingly, the amount of labor required to attach the tibial insert trial 18 to a patient can be further reduced.

Also, according to the present embodiment, the first connection mechanism 46 can prevent the keel punch handle 17 from coming out from the keel punch 16. Also, the keel punch handle 17 can be disconnected from the keel punch 16 when necessary. This makes it possible to suppress the case where the keel punch handle 17 and the keel punch 16 become hindrances. As a result, the amount of labor required to attach the tibial insert trial 18 to a patient can be further reduced.

According to the present embodiment, connection and disconnection between the keel punch handle 17 and the keel punch 16 can be performed with a simple configuration in which the keel punch handle 17 and the keel punch 16 are relatively moved in the first direction D1. This makes it possible to further reduce the amount of labor required to attach the tibial insert trial 18 to a patient.

According to the present embodiment, the first direction D1 is a rotational direction around an axis parallel to the axial direction of the keel punch handle 17. According to this configuration, connection and disconnection between the keel punch handle 17 and the keel punch 16 can be performed with a simple configuration in which the keel punch handle 17 and the keel punch 16 are relatively rotated. This makes it possible to further reduce the amount of labor required to attach the tibial insert trial 18 to a patient.

According to the present embodiment, connection and disconnection between the first protrusion 46a and the first projections 46b can be performed with a simple operation, that is, relative movement of the keel punch handle 17 and the keel punch 16.

According to the present embodiment, the keel punch handle 17 can be connected to the keel punch 16 by causing the first protrusion 46a, which has a protruding shape, to be caught on the first projections 46b formed within the tubular portion 161 of the keel punch 16. Also, the aforementioned connection can be canceled by rotating the first protrusion 46a relative to the first projections 46b.

According to the present embodiment, since the first protrusion 46a can be received by the pair of projections 46b, the connection strength between the keel punch handle 17 and the keel punch 16 can be further increased. With this configuration, the operator does not need to pay attention to the connection strength between the keel punch handle 17 and the keel punch 16 when handling the keel punch handle 17 to which the keel punch 16 has been attached. As a result, the amount of labor required to attach the tibial insert trial 18 to a patient can be further reduced.

According to the present embodiment, the second connection mechanism 47 enables the keel punch handle 17 and the keel punch 13 to be integrally connected. This makes it possible to pull out the keel punch guide 13 using the keel punch handle 17. Also, the keel punch handle 17 can be disconnected from the keel punch guide 13 when necessary. This makes it possible to suppress the case where the keel punch handle 17 and the keel punch guide 13 become hindrances. As a result, the amount of labor required to attach the tibial insert trial 18 to a patient can be further reduced.

According to the present embodiment, connection and disconnection between the keel punch handle 17 and the keel punch guide 13 can be performed with a simple configuration in which the keel punch handle 17 and the keel punch guide 13 are relatively moved in the second direction D2. This makes it possible to further reduce the amount of labor required to attach the tibial insert trial 18 to a patient.

According to the present embodiment, the second direction D2 is a rotational direction around an axis parallel to the axial direction of the keel punch handle 17. According to this configuration, connection and disconnection between the keel punch handle 17 and the keel punch guide 13 can be performed with a simple configuration in which the keel punch handle 17 and the keel punch guide 13 are relatively rotated. This makes it possible to further reduce the amount of labor required to attach the tibial insert trial 18 to a patient.

According to the present embodiment, connection and disconnection between the second protrusions 47a and the second connected portions 47b and 47c can be performed with a simple operation, that is, relative movement of the keel punch handle 17 and the keel punch guide 13.

According to the present embodiment, a single motion to displace the keel punch handle 17 in one direction (the first disconnecting direction D12 and the second connecting direction D21) relative to the keel punch 16 and the keel punch guide 13 makes it possible to simultaneously cancel the connection between the keel punch handle 17 and the keel punch 16 through the first connection mechanism 46 and connect the keel punch handle 17 to the keel punch guide 13 through the second connection mechanism 47. This makes it possible to further reduce the amount of labor required to attach the tibial insert trial 18 to a patient, through a reduction in the amount of labor in handling the keel punch handle 17.

According to the present embodiment, the first connecting direction D11 and the second connecting direction D21 are set to opposite directions. According to this configuration, a configuration can be realized that makes it possible to simultaneously perform an operation to cancel the connection between the keel punch handle 17 and the keel punch 16 through the first connection mechanism 46 and an operation to connect the keel punch handle 17 to the keel punch guide 13 through the second connection mechanism 47. It is thus possible to further reduce the amount of labor required to attach the tibial insert trial 18 to a patient, through a reduction in the amount of labor in handling the keel punch handle 17.

According to the present embodiment, even in a state in which the space around the tibia 100 is small because the template 12 has been attached to the patient's tibia 100, the connecting portion 11d of the template handle 11 can be removed from the template 12 through the passage 37 in the keel punch guide 13. This makes it possible to more easily operate the template handle 11. Accordingly, the amount of labor required to attach the tibial insert trial 18 to a patient can be further reduced.

According to the present embodiment, the spacer 19 for adjusting the height of the tibial insert trial 18 from the template 12 is included in the tibial trial attachment instrument assembly 2. This eliminates the need for a laborious operation to prepare the spacer 19, separately from other members of the tibial trial attachment instrument assembly 2. Accordingly, the amount of labor required to attach the tibial insert trial 18 to a patient can be further reduced.

According to the present embodiment, the first connection mechanism 46 for connecting the keel punch handle 17 to the keel punch 16 is arranged within the tubular portion 161 of the keel punch 16 that is to be inserted into the patient's tibia 100. Since the tubular portion 161 is configured to be inserted into the tibia 100, the length of the tubular portion 161 in the axial direction and the diameter thereof can be secured to some extent. This makes it possible to sufficiently secure the space for arranging the first connection mechanism 46 within the tubular portion 161. Accordingly, the first connection mechanism 46 can be formed to have a size that makes it possible to sufficiently secure the connection strength between the keel punch handle 17 and the keel punch 16. Furthermore, the degree of freedom in designing of the structure (the first connection mechanism 46) for connecting the keel punch handle 17 to the keel punch 16 can be further increased.

According to the present embodiment, the first protrusion 46*a* can be connected to the first projections 46*b* by inserting the insertion end portion 45 of the keel punch handle 17 into the tubular portion 161. This simple configuration of the first connection mechanism 46 makes it possible to form the first connection mechanism 46 to have a size with which the connection strength between the keel punch handle 17 and the keel punch 16 can be secured sufficiently. Furthermore, the degree of freedom in designing of the structure (the first connection mechanism 46) for connecting the keel punch handle 17 to the keel punch 16 can be further increased.

According to the present embodiment, connection and disconnection between the first protrusion 46*a* and the first projections 46*b* can be performed with a simple configuration in which the keel punch handle 17 and the keel punch 16 are relatively displaced.

According to the present embodiment, the first connection mechanism 46 has a connection structure using a protrusion (the first protrusion 46*a*). This configuration makes it possible to further increase the strength of the first protrusion 46*a* in the first connection mechanism 46, by employing a simple protruding shape.

According to the present embodiment, since the first protrusion 46*a* can be received by the pair of projections 46*b*, the connection strength between the keel punch handle 17 and the keel punch 16 can be further increased.

According to the present embodiment, connection between the keel punch handle 17 and the keel punch 16 through the first connection mechanism 46 can be realized by inserting the keel punch handle 17 into the keel punch 16 until the first stopper 40 of the keel punch handle 17 is received by the opening edge portion 161*a* of the tubular portion 161, and thereafter displacing the keel punch handle 17 relative to the keel punch 16. Thus, the amount of insertion of the keel punch handle 17 into the keel punch 16 can be defined by the second stopper 44.

According to the present embodiment, only a single component, namely the spacer 19, is needed to adjust the height position of the tibial insert trial 18 from the template 12. This makes it possible to further reduce the number of components in the configuration of the artificial knee joint replacement operation instrument 1 for adjusting the height position of the tibial insert trial 18. Also, the spacer 19 is arranged in a partial area of the template 12 in the inward-outward direction X1 of a patient, and in the central portion 20 of the template 12. This makes it possible to shorten the length over which the spacer 19 comes into contact with the template 12 and the tibial insert trial 18 in the inward-outward direction X1. Accordingly, when an operator inserts the spacer 19 between the template 12 and the tibial insert trial 18, the frictional resistance that the spacer 19 is subjected to can be further reduced. This makes it possible to further reduce the amount of labor required to attach the tibial insert trial 18 to a patient.

According to the present embodiment, the leading end portion of the spacer 19 in the inserting direction includes the tapered portions 64A and 64B, which are formed into tapered shapes. This configuration makes it possible to further reduce the force required to insert the spacer 19 between the template 12 and the tibial insert trial 18. Accordingly, the amount of labor required to attach the tibial insert trial 18 to a patient can be further reduced.

According to the present embodiment, in the inward-outward direction X1, the length of the insertion space 57 between the template 12 and the tibial insert trial 18 is set larger than the length of the spacer 19. According to this configuration, the spacer 19 does not need to be strictly positioned in the inward-outward direction X1 relative to the spacer insertion space 57 when the spacer 19 is inserted into the insertion space 57, for example. This makes it possible to further reduce the amount of labor required to attach the tibial insert trial 18 to a patient.

According to the present embodiment, when the spacer 19 is inserted between the template 12 and the tibial insert trial 18, the spacer 19 can be inserted more accurately by being guided by the rails 58A and 58B.

According to the present embodiment, the tilt restriction mechanism 70 is provided. According to this configuration, the tibial insert trial 18 can be restricted from tilting by joining the template 12 to the tibial insert trial 18 via the spacer 19. This makes it possible to further reduce the amount of labor required by an operator to maintain the orientation of the tibial insert trial 18 on the template 12. As a result, the amount of labor required to attach the tibial insert trial 18 to a patient can be further reduced.

According to the present embodiment, the stopper 63 that defines the position of the spacer 19 is formed at a front end of the spacer 19. Since this stopper 63 is accommodated in the cutout portion 18*c* of the tibial insert trial 18, the stopper 63 does not become a hindrance around the template 12 when being accommodated between the template 12 and the tibial insert trial 18. Also, the stopper 63 can also be used as a portion of the tilt restriction mechanism 70, which makes it possible to prevent the shape of the tibial insert trial 18 in its periphery from becoming complex. This makes it possible to further reduce the amount of labor required to attach the tibial insert trial 18 to a patient.

According to the present embodiment, the position shift restriction mechanism 80 is provided. According to this configuration, engagement between the first shift restriction portion 81 with the second shift restriction portion 82 can restrict the position of the tibial insert trial 18 from being shifted in the inward-outward direction X1 relative to the template 12. This makes it possible to further reduce the amount of labor required by an operator to maintain the orientation of the tibial insert trial 18 on the template 12. As a result, the amount of labor required to attach the tibial insert trial 18 to a patient can be further reduced.

According to the present embodiment, in the inward-outward direction X1, the positions of the fixing pin insertion hole portions 30*a* to 30*f* in the template 12 differ from the position of the spacer 19. According to this configuration, the fixing pins 31 do not become hindrances when the spacer 19 is inserted between the template 12 and the tibial insert trial 18 in a state in which the template 12 has been fixed to the tibial 100 with the fixing pins 31. Accordingly, the fixing pins 31 do not need to be removed from the template 12 during a height adjustment operation performed using the spacer 19, and the amount of labor required to attach the tibial insert trial 18 to a patient can be further reduced.

Although an embodiment of the present invention has been described thus far, the present invention is not limited to the above-described embodiment, and various modifications can be made within the scope recited in the claims. For example, the following modifications are possible.

In the above embodiment, the first direction D1 and the second direction D2, which are rotational directions, have been described as examples of the directions in which the first connection mechanism 46 and the second connection mechanism 47 are operated. However, this need not be the case. For example, the first direction D1 and the second direction D2 may alternatively be helical directions, or may be straight directions. Also, a configuration may also be employed in which a lever that passes from a base end to a leading end of the keel punch handle is provided, and the keel punch handle is connected to or disconnected from the inside of the tubular portion of the keel punch by displacing this lever upward or downward.

INDUSTRIAL APPLICABILITY

The present invention is broadly applicable as an artificial knee joint replacement operation instrument used in an operation for replacing a patient's knee joint with an artificial knee joint.

DESCRIPTIONS OF REFERENCE NUMERALS

1 Artificial knee joint replacement operation instrument
2 Tibial trial attachment instrument assembly
11 Template handle
12 Template
13 Keel punch guide
16 Keel punch
17 Keel punch handle
18 Tibial insert trial
19 Spacer
37 Passage
46 First connection mechanism
46a First protrusion
46b First projection (first connected portion)
47 Second connection mechanism
47a Second protrusion
47b, 47c Second connected portion
100 Tibia
131 Tubular portion of keel punch guide
161 Tubular portion of keel punch
D1 First direction
D2 Second direction

The invention claimed is:

1. An artificial knee joint replacement operation instrument comprising:
a tibial trial attachment instrument assembly to be used in an operation for replacing a patient's knee joint with an artificial knee joint,
the tibial trial attachment instrument assembly including:
a template to be attached to the patient's tibia;
a keel punch guide to be joined to the tibia via the template;
a keel punch to be inserted into the tibia through the keel punch guide;
a keel punch handle for operating the keel punch; and
a tibial insert trial to be placed on the template, the tibial insert trial being separate from the template,
wherein the tibial trial attachment instrument assembly further comprising:
a first connection mechanism configured to enable the keel punch handle and the keel punch to be attached to and detached from each other, and prevent the keel punch handle from coming out from the keel punch,
wherein the first connection mechanism is further configured to connect and disconnect the keel punch handle to and from the keel punch by moving the keel punch handle relative to the keel punch in a predetermined first direction that differs from an axial direction of the keel punch handle, and
wherein the first direction is a rotational direction around an axis parallel to the axial direction.

2. The artificial knee joint replacement operation instrument according to claim 1,
wherein the keel punch guide includes a tubular portion that is provided to allow the keel punch to pass therethrough and is arranged in alignment with the template, and
a passage through which a template handle for operating the template passes when the template handle is removed from the template is formed in an outer-circumferential portion of the tubular portion.

3. The artificial knee joint replacement operation instrument according to claim 1,
wherein the tibial trial attachment instrument assembly includes a spacer capable of being inserted between the tibial insert trial and the template.

4. An artificial knee joint replacement operation instrument comprising:
a tibial trial attachment instrument assembly to be used in an operation for replacing a patient's knee joint with an artificial knee joint,
the tibial trial attachment instrument assembly including:
a template to be attached to the patient's tibia;
a keel punch guide to be joined to the tibia via the template;
a keel punch to be inserted into the tibia through the keel punch guide;
a keel punch handle for operating the keel punch; and
a tibial insert trial to be placed on the template, the tibial insert trial being separate from the template,
wherein the tibial trial attachment instrument assembly further comprising:
a first connection mechanism configured to enable the keel punch handle and the keel punch to be attached to and detached from each other, and prevent the keel punch handle from coming out from the keel punch,
wherein the first connection mechanism has a first protrusion formed in one of the keel punch handle and the keel punch, and a first connected portion formed in the other one of the keel punch handle and the keel punch, and
the first protrusion is connected to and disconnected from the first connected portion by relative movement of the keel punch handle and the keel punch,
wherein the first protrusion is provided at a leading end of the keel punch handle, and has a rectangular shape in a cross-section orthogonal to an axial direction of the keel punch handle, and
the first connected portion includes a first projection formed on an inner-circumferential face of a tubular portion of the keel punch, and
wherein a pair of first projections is provided at a pitch of 180 degrees on the inner-circumferential face of the tubular portion, and a hole portion having a cross-sectional shape that matches a cross-sectional shape of the first protrusion is formed within the tubular portion.

5. An artificial knee joint replacement operation instrument comprising:
a tibial trial attachment instrument assembly to be used in an operation for replacing a patient's knee joint with an artificial knee joint,
the tibial trial attachment instrument assembly including:
a template to be attached to the patient's tibia;
a keel punch guide to be joined to the tibia via the template;
a keel punch to be inserted into the tibia through the keel punch guide;
a keel punch handle for operating the keel punch; and
a tibial insert trial to be placed on the template, the tibial insert trial being separate from the template,
wherein the tibial trial attachment instrument assembly further comprising:
a second connection mechanism for enabling the keel punch handle and the keel punch guide to be attached to and detached from each other, and integrally connecting the keel punch handle to the keel punch guide,
wherein the second connection mechanism is configured to connect and disconnect the keel punch handle to and from the keel punch guide by moving the keel punch handle relative to the keel punch guide in a predetermined second direction that differs from an axial direction of the keel punch handle, and
wherein the second direction is a rotational direction around an axis parallel to the axial direction.

6. The artificial knee joint replacement operation instrument according to claim 5,
wherein the second connection mechanism includes a second protrusion formed in one of the keel punch handle and the keel punch guide, and a second connected portion formed in the other one of the keel punch handle and the keel punch guide, and
the second protrusion is connected to and disconnected from the second connected portion by relative movement of the keel punch handle and the keel punch guide.

7. An artificial knee joint replacement operation instrument comprising:
a tibial trial attachment instrument assembly to be used in an operation for replacing a patient's knee joint with an artificial knee joint,
the tibial trial attachment instrument assembly including:
a template to be attached to the patient's tibia;
a keel punch guide to be joined to the tibia via the template;
a keel punch to be inserted into the tibia through the keel punch guide;
a keel punch handle for operating the keel punch; and
a tibial insert trial to be placed on the template, the tibial insert trial being separate from the template,
wherein the tibial trial attachment instrument assembly further includes:
a first connection mechanism configured to enable the keel punch handle and the keel punch to be attached to and detached from each other, and prevent the keel punch handle from coming out from the keel punch; and
a second connection mechanism for enabling the keel punch handle and the keel punch guide to be attached to and detached from each other, and integrally connecting the keel punch handle to the keel punch guide,
further wherein displacing the keel punch handle in one direction relative to the keel punch and the keel punch guide cancels a connection between the keel punch handle and the keel punch through the first connection mechanism, and connects the keel punch handle to the keel punch guide through the second connection mechanism, and
wherein a first direction in which the keel punch handle is displaced relative to the keel punch to connect the keel punch handle to the keel punch through the first connection mechanism and a second direction in which the keel punch handle is displaced relative to the keel punch guide to connect the keel punch handle to the keel punch guide through the second connection mechanism are set to opposite directions.

* * * * *